(12) United States Patent
Ishikawa

(10) Patent No.: US 12,083,354 B2
(45) Date of Patent: Sep. 10, 2024

(54) TREATMENT SUPPORT DEVICE

(71) Applicant: SHIMADZU CORPORATION, Kyoto (JP)

(72) Inventor: Akihiro Ishikawa, Kyoto (JP)

(73) Assignee: SHIMADZU CORPORATION, Kyoto (JP)

(*) Notice: Subject to any disclaimer, the term of this patent is extended or adjusted under 35 U.S.C. 154(b) by 89 days.

(21) Appl. No.: 17/495,297

(22) Filed: Oct. 6, 2021

(65) Prior Publication Data

US 2022/0118272 A1 Apr. 21, 2022

(30) Foreign Application Priority Data

Oct. 19, 2020 (JP) ................... 2020-175600

(51) Int. Cl.
*A61N 5/06* (2006.01)
*A61N 5/067* (2006.01)

(52) U.S. Cl.
CPC ............. *A61N 5/062* (2013.01); *A61N 5/067* (2021.08); *A61N 2005/0652* (2013.01); *A61N 2005/0662* (2013.01)

(58) Field of Classification Search
CPC ...... A61N 5/06; A61N 5/0613; A61N 5/0616; A61N 5/062; A61N 2005/0626; A61N 2005/0642; A61N 2005/0643; A61N 2005/0651; A61N 5/067

USPC ....................................... 607/88–91
See application file for complete search history.

(56) References Cited

U.S. PATENT DOCUMENTS

| 11,931,008 B2* | 3/2024 | Ishikawa | A61B 5/0037 |
| 2017/0032521 A1* | 2/2017 | Kubo | A61B 1/00009 |
| 2021/0059532 A1* | 3/2021 | Tsumatori | A61B 5/0084 |
| 2022/0054855 A1* | 2/2022 | Ishikawa | A61B 5/4848 |
| 2022/0212025 A1* | 7/2022 | Ishikawa | A61N 5/062 |
| 2022/0288411 A1* | 9/2022 | Tsumatori | A61N 5/0613 |

FOREIGN PATENT DOCUMENTS

| WO | 2019215905 A1 | 11/2019 | |
| WO | WO-2021038913 A1 * | 3/2021 | ......... A61B 1/00186 |

* cited by examiner

*Primary Examiner* — Ahmed M Farah
(74) *Attorney, Agent, or Firm* — Muir Patent Law, PLLC

(57) ABSTRACT

A treatment support device is provided with an irradiation unit, a fluorescence detection unit, and a change acquisition unit for acquiring a change degree of a fluorescence signal detected within a first time range within a treatment time. The treatment support device is provided with: a determination unit for determining whether or not the progress of the treatment is in a steady state based on the fact that the change degree of the fluorescence signal within the first time range falls within a predetermined range of the change degree; and an operation control unit for performing predetermined operation control when the progress of the treatment is determined to be in the steady state by the determination unit.

10 Claims, 17 Drawing Sheets

TREATMENT SUPPORT DEVICE

CROSS-REFERENCE TO RELATED APPLICATIONS

The priority application number JP2020-175600, entitled "Treatment Support Device" filed on Oct. 19, 2020, invented by Akihiro Ishikawa upon which this patent application is based is hereby incorporated by reference.

BACKGROUND OF THE INVENTION

Technical Field

The present invention relates to a treatment support device.

Description of the Background Art

Conventionally, a treatment support device is known in which a support of a treatment (photoimmunotherapy) for killing cancer cells by emitting treatment light in a predetermined wavelength range to a medical agent containing a fluorescent material administered to a body of a subject or the treatment is performed. Such a treatment support device is disclosed, for example, in WO 2019/215905.

WO 2019/215905 discloses a treatment support device provided with a fluorescence detection unit for detecting fluorescence and a fluorescence image generation unit for generating a fluorescence image based on a fluorescence signal output by the fluorescence detection unit. The fluorescence detection unit detects the fluorescence emitted by the fluorescent material of the medical agent administered to a body of a subject for treatment by photoimmunotherapy. The treatment support device described in WO 2019/215905 is configured to output a fluorescence image generated by the fluorescence image generation unit before the treatment and a fluorescence image generated by the fluorescence image generation unit at the time of the treatment. In the treatment support device described in WO 2019/215905, a user, such as, e.g., a doctor, confirms the progress of the treatment to cancer cells by the change in the detected fluorescence by comparing the fluorescence image before the treatment with the fluorescence image at the time of the treatment.

Further, although not specifically described in WO 2019/215905, a conventional treatment support device as described in WO 2019/215905 acquires the change in the fluorescence signal value together with the fluorescence image in order to confirm the progress of the treatment by photoimmunotherapy Here, a user, such as, e.g., a doctor, must determine the progress of the treatment by the photoimmunotherapy from the comparison between the fluorescence image before the treatment and the fluorescence image at the time of the treatment, or the change in the acquired fluorescence signal value. However, even during the treatment, the detected fluorescence signal value will not be completely nulled because the medical agent containing the fluorescent material is newly transported to the treatment site by the blood flow. Therefore, it is difficult to easily determine the completion of the treatment by photoimmunotherapy from the fluorescence image or the change in the fluorescence signal value. For this reason, there is a need for a treatment support device that allows a user, such as, e.g., a doctor, to easily determine the completion of the treatment by photoimmunotherapy.

The present invention has been made to solve the aforementioned problems. It is an object of the present invention to provide a treatment support device capable for a user, such as, e.g., a doctor, to easily determine completion of treatment by photoimmunotherapy.

SUMMARY OF THE INVENTION

A treatment support device according to one aspect of the present invention, includes:
   an irradiation unit configured to irradiate a medical agent with treatment light in treatment for killing cancer cells by irradiating the medical agent with the treatment light of a predetermined wavelength, the medical agent including a fluorescent material administered to a body of a subject;
   a fluorescence detection unit configured to detect fluorescence emitted by the fluorescent material of the medical agent excited by irradiation of the treatment light;
   a change acquisition unit configured to acquire a change degree of a fluorescence signal detected by the fluorescence detection unit in a first time range within a treatment time;
   a determination unit configured to determine whether or not a progress of the treatment is in a steady state, based on at least a fact that the change degree of the fluorescence signal within the first time range acquired by the change acquisition unit has fallen within a predetermined range of the change degree; and
   an operation control unit configured to control a predetermined operation related to a fact that the treatment is in the steady state when it is determined by the determination unit that the progress of the treatment is in the steady state.

The term "steady state" means a state in which, as the elapse of the treatment time (irradiation time of the treatment light), based on irradiation of treatment light of a predetermined wavelength range to a medical agent containing a fluorescent material administered to a body of a subject, the treatment for killing cancer cells (treatment by photoimmunotherapy) progresses, the change in the fluorescence (fluorescence signal value) emitted from a fluorescent material of a medical agent administered to a body of a subject decreased, and therefore it is considered that the treatment has been sufficiently performed.

The treatment support device according to one aspect of the present invention acquires the change degree of the fluorescence signal detected by the fluorescence detection unit within a first time range within the treatment time by the change acquisition unit. In a case where it is determined by the determination unit that the progress of the treatment is in a steady state based on the fact that the change degree of the fluorescence signal within the first time range acquired by at least the change acquisition unit has fallen within a predetermined range of the change degree, the operation control unit controls a predetermined operation related that the treatment is in the steady state. With this, a user, such as, e.g., a doctor, can recognize that it has become in a state (steady state) in which the treatment is deemed to have been performed sufficiently from the fact that the predetermined operation has been performed by the operation control unit. As a result, it is possible to provide a treatment support device capable for a user, such as, e.g., a doctor, to easily determine completion of treatment (treatment by photoimmunotherapy) for killing cancer cells by irradiating a medical agent including a fluorescent material administered to a body of a subject with treatment light in a predetermined wavelength range.

DESCRIPTION OF THE PREFERRED EMBODIMENT

Hereinafter, some embodiments in which the present invention is embodied will be described with reference to the attached drawings.

First Embodiment

Referring to FIGS. 1 to 14, a configuration of a treatment support device 100 according to a first embodiment of the present invention will be described.

(Configuration of Treatment Support Device)

Figure 1:
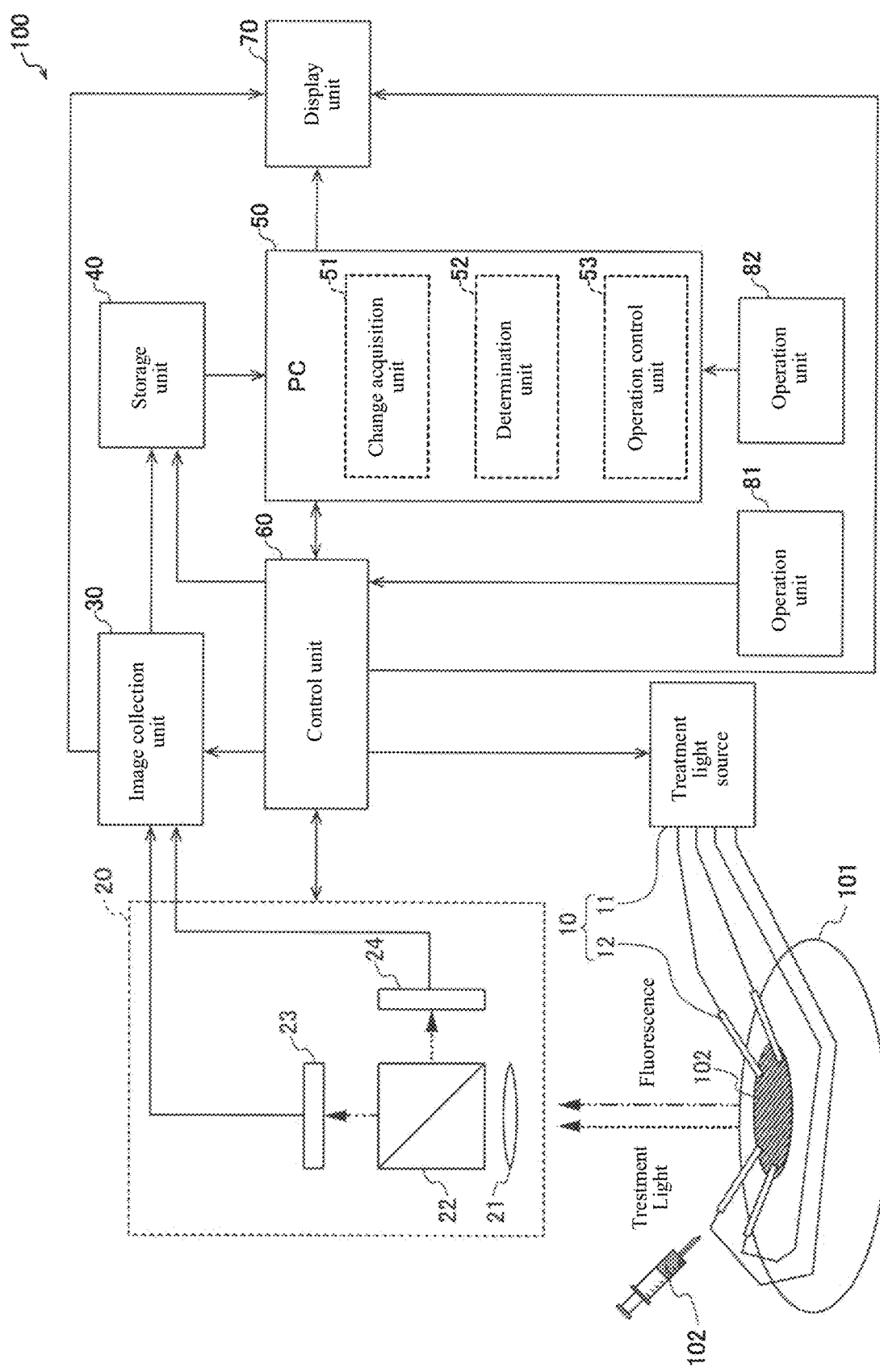
FIG. 1 is a block diagram showing an overall configuration of a treatment support device according to a first embodiment of the present invention.

The treatment support device 100 according to the first embodiment is a device for supporting treatment in photoimmunotherapy. Specifically, as shown in FIG. 1, the treatment support device 100 is configured to irradiate the cancer patient 101 with the treatment light (excitation light) and detect the fluorescence emitted from the fluorescent material of the medical agent 102 administered to the body of the cancer patient 101. In addition to the support of the treatment by photoimmunotherapy, the treatment support device 100 is configured such that treatment by photoimmunotherapy can be performed by continuously emitting treatment light in a specific wavelength band according to the fluorescent material of the medical agent 102. That is, the treatment support device 100 of the first embodiment is also a treatment device by photoimmunotherapy.

Note that the cancer patient 101 is an example of the "subject" recited in claims. The cancer patient 101 may be an animal other than a human.

As shown in FIG. 1, the treatment support device 100 is provided with an irradiation unit 10, a light detection unit 20, an image collection unit 30, and a storage unit 40.

(Configuration of Irradiation Unit)

The irradiation unit 10 is configured to irradiate the medical agent 102 with treatment light in the treatment (treatment by photoimmunotherapy) for killing cancer cells by irradiating the medical agent 102 containing a fluorescent material administered to the body of the cancer patient 101 with the treatment light in a predetermined wavelength range. That is, the irradiation unit 10 is configured to emit the treatment light (excitation light) to the medical agent 102 containing the fluorescent material administered to the body of the cancer patient 101 in the treatment by the photoimmunotherapy. The irradiation unit 10 includes a treatment light source 11 and a plurality of treatment probes 12 as shown in FIG. 1.

The treatment light source 11 is configured to emit the treatment light (excitation light) in a specific wavelength range for exciting the fluorescent material contained in the medical agent 102. The treatment light source 11 includes a laser diode (LD), a light-emitting diode (LED), or the like.

The treatment probe 12 is configured to be inserted into the body of the cancer patient 101 to emit the treatment light in the body of the cancer patient 101. The treatment probe 12 includes an optical fiber for guiding the light from the treatment light source 11. The treatment probe 12 is inserted along a cylindrical guide (not shown), such as diffuser, formed by a transparent member, such as, e.g., a glass, to be inserted into the body of the cancer patient 101 toward a position (treatment site) that is a treatment point in the body of the cancer patient 101.

A user, such as, e.g., a doctor, grasps the position of the cancer in advance using an MRI (Magnetic Resonance Image), an X-ray CT (Computed Tomography), an ultrasonic wave echo, or the like. Then, the user, such as, e.g., a doctor, inserts the treatment probe 12 into the body of the cancer patient 101 while confirming the position of the cancer by an ultrasonic wave echo or the like. The treatment probe 12 is configured to guide and emit the treatment light from the treatment light source 11 in the body of the cancer patient 101. With this, the fluorescent material of the medical agent 102 is excited by the treatment light.

The treatment support device 100 can perform the treatment (photoimmunotherapy) for killing cancer cells by continuously emitting treatment light, which is treatment light in a particular wavelength range for exciting the fluorescent material contained in the medical agent 102, within the body of the cancer patient 101 by the treatment probe 12.

Here, in the photoimmunotherapy, the medical agent 102 (see FIG. 1) is administered to the body of the cancer patient 101 (see FIG. 1) before emitting the treatment light. The medical agent 102 contains a fluorescent material that emits fluorescence and an antibody. The fluorescent material of the medical agent 102 is a substance that is excited to emit fluorescence by being irradiated with treatment light and a substance that causes a photochemical reaction by being continuously irradiated with treatment light. The fluorescent material is a chemical substance, such as, e.g., an IRDye (registered mark) 700DX.

At the time of treatment by photoimmunotherapy, the irradiation unit 10 emits treatment light corresponding to the type of the fluorescent material of the medical agent 102 administered to the cancer patient 101 to the treatment site (cancer cell) of the cancer patient 101.

Note that the treatment light to be emitted by the irradiation unit 10 during the treatment is a light in a wavelength range in which the fluorescent material of the medical agent 102 used for the treatment causes a photochemical reaction in a wavelength region of 600 nm or more and 2,500 nm or less, which is a region of near-infrared light from a part of visible light. The treatment light varies depending on the type of the fluorescent material of the medical agent 102 used for the treatment. For example, in a case where IRDye 700DX is used for the fluorescent material of the medical agent 102, the irradiation unit 10 emits the light having a peak position of a wavelength of 600 nm or more and 700 nm or less, for example, non-thermal red light (near-infrared light) having a peak position of a wavelength of about 690 nm, during the treatment by the photoimmunotherapy.

(Configuration of Light Detection Unit)

The light detection unit 20 is configured to detect the treatment light and the fluorescence. The light detection unit 20 is provided with a lens 21 and a prism 22, as shown in FIG. 1. The light detection unit 20 includes a fluorescence detection unit 23 and a treatment light detection unit 24.

The lens 21 is configured such that the fluorescence emitted by the fluorescent material of the medical agent 102 and the visible light containing the treatment light emitted by the irradiation unit 10 are incident. The fluorescence and the visible light including the treatment light incident on the lens 21 are converged by the lens 21 and incident on the prism 22.

The prism 22 is configured to separate the incident light, and the fluorescence and the visible light including the treatment light incident on the lens 21 are separated by the prism 22. The fluorescence separated by the prism 22 is configured to be imaged at the fluorescence detection unit 23. The visible light containing the treatment light separated by the prism 22 is configured to be imaged at the treatment light detection unit 24.

The fluorescence detection unit 23 is configured to detect the fluorescence emitted by the fluorescent material of the medical agent 102 excited by the irradiation of the treatment light. The fluorescence detection unit 23 includes an image sensor for capturing an image based on the fluorescence emitted by the fluorescent material of the medical agent 102 separated by the prism 22. The imaging element photoelectrically converts the fluorescence into an electric signal. The image sensor is, for example, a CMOS (Complementary Metal Oxide Semiconductor) image sensor, or a CCD (Charge Coupled Device) image sensor.

In other words, the fluorescence detection unit 23 is configured to detect the fluorescence emitted by the fluorescent material of the medical agent 102 excited by the irradiation of the treatment light and acquire (capture) the fluorescence image 71 (see FIG. 2) based on the detected fluorescence. Note that the fluorescence image 71 is an image representing the distribution state of the fluorescence (distribution 71a of the fluorescence) emitted by the fluorescent material of the medical agent 102.

The fluorescence detection unit 23 is configured to selectively detect the light in the region including the wavelength range of the fluorescence emitted by the fluorescent material of the medical agent 102 by the wavelength-selectivity of the optical filter. For example, when IRDye700DX is used for the fluorescent material of the medical agent 102, the fluorescence detection unit 23 is configured to detect the fluorescence and capture the fluorescence image 71 based on the light having a wavelength of 700 nm or more by the wavelength-selectivity of the optical filter.

Note that the IRDye 700DX is excited by the light having a wavelength of 600 nm or more and 700 nm or less and emits the light having a peak at a wavelength of about 700 nm or 770 nm as fluorescence.

The treatment light detection unit 24 is configured to detect the visible light including the treatment light. The treatment light detection unit 24 includes an image sensor that detects the visible light containing the treatment light separated by the prism 22 and captures the image based on the visible light containing the detected treatment light. The image sensor photoelectrically converts the visible light including the treatment light into an electric signal. The imaging element is, for example, a CMOS image sensor, a CCD image sensor, or the like.

The treatment light detection unit 24 is configured to selectively detect the light in the region including the wavelength range of the treatment light emitted by the irradiation unit 10 (treatment probe 12) by the wavelength-selectivity of the optical filter. When light having a wavelength of 600 nm or more and 700 nm or less, for example, non-thermal red light having a wavelength peak position of about 690 nm is emitted at the time of the treatment by photoimmunotherapy, the treatment light detection unit 24 is configured to detect the visible light including the treatment light based on the light having a wavelength of 400 nm or more and 700 nm or less including the wavelength range of the treatment light and the wavelength range of visible light by the wavelength-selectivity of the optical filter and capture the visible light image 72 (see FIG. 3). That is, the visible light image 72 includes an image (treatment light image) based on the light in the wavelength range of the treatment light ad detections. Further, the visible light image 72 is a color image captured based on the light in the wavelength range of the treatment light and the visible light.

(Configuration of Image Collection Unit)

The image collection unit 30 (see FIG. 1) includes a processor, such as a GPU (Graphics Processing Unit), or an FPGA (Field-Programmable Gate Array) configured for imaging.

The image collection unit 30 is configured to receive the fluorescence signal detected by the fluorescence detection unit 23 and the signal of the visible light including the treatment light detected by the treatment light detection unit 24, as electric signals. That is, the image data of the fluorescence image 71 (see FIG. 2) captured by the fluorescence detection unit 23 and the image data of the visible light image 72 (see FIG. 3) captured by the treatment light detection unit 24 are input as electric signals. The image collection unit 30 is configured to collect visible light signals (data of the fluorescence image 71 and the visible light image 72) including the fluorescence signal and the treatment light based on the time series. The image collection unit 30 is configured to collect the fluorescence signal or stop the collection of the fluorescence signal and collect the visible light signals or stop the collection, under the control of the control unit 60, which will be described later.

(Configuration of Storage Unit)

The storage unit 40 (see FIG. 1) is configured to store (save) the fluorescence signal of the fluorescence detected by the light detection unit 20 (fluorescence detection unit 23). The storage unit 40 is configured to store (save) the signal of the visible light including the treatment light detected by the light detection unit 20 (treatment light detection unit 24). The storage unit 40 is configured to store (save) the visible light signals (data of the fluorescence image 71 and the visible light image 72) including the fluorescence signal and the treatment light collected by the image collection unit 30. The storage unit 40 stores (saves) the visible light signals (data of the fluorescence image 71 and the visible light image 72) including, for example, the fluorescence signal and the treatment light collected by the image collection unit 30 based on time series, together with the time stamps such as imaging date and time.

The storage unit 40 includes, for example, a nonvolatile memory, a hard disk drive (HDD: Hard Disk Drive), an SSD (Solid State Drive), and the like. As a result, the storage unit 40 can save (store) for a long-term the fluorescence signal of the fluorescence detected by the light detection unit 20 (fluorescence detection unit 23) and the signal of the visible light including the treatment light detected by the light detection unit 20 (treatment light detection unit 24). Note that the storage unit 40 may include a database connected by a network provided outside the treatment support device 100.

As shown in FIG. 1, the treatment support device 100 is provided with a personal computer (Personal Computer) 50, a control unit 60, a display unit 70, an operation unit 81, and an operation unit 82.

(Configuration of PC)

The PC 50 (see FIG. 1) is a computer including a CPU (Central Processing Unit), a ROM (Read Only Memory), a RAM (Random Access Memory), and the like. Note that the PC 50 is an example of the "analysis unit" recited in claims.

The PC 50 is configured to analyze the fluorescence signal collected by the image collection unit 30 and the visible light signal including the treatment light (data of the fluorescence image 71 and the visible light image 72). That is, the PC 50 is configured to analyze the fluorescence signal (fluorescence signal value) detected by the fluorescence detection unit 23. The PC 50 is configured to analyze the fluorescence signal value on a time series basis. Further, the PC 50 is configured to analyze the signal value of the visible light containing the treatment light detected by the treatment light detection unit 24.

The PC 50 includes, as functional components, a change acquisition unit 51, a determination unit 52, and an operation control unit 53. That is, the PC 50 functions as the change acquisition unit 51, the determination unit 52, and the operation control unit 53, by executing programs. The change acquisition unit 51, the determination unit 52, and the operation control unit 53 are functional blocks as the software in the PC 50, and are configured to function based on the command signal of the PC 50 as hardware.

As will be described later, the change acquisition unit 51 calculates (acquires) the change degree of the fluorescence signal detected by the fluorescence detection unit 23 in the time range Q within the treatment time. Note that the time range Q is an example of the "first time range" recited in claims.

Further, the change acquisition unit 51 calculates (acquires) the change rate v1, which is the change rate of the fluorescence signal within the time range Q (see FIG. 7) detected by the fluorescence detection unit 23, as the change degree of the fluorescence signal. Note that the change rate v1 is an example of the "first change rate" recited in claims.

Figure 7:
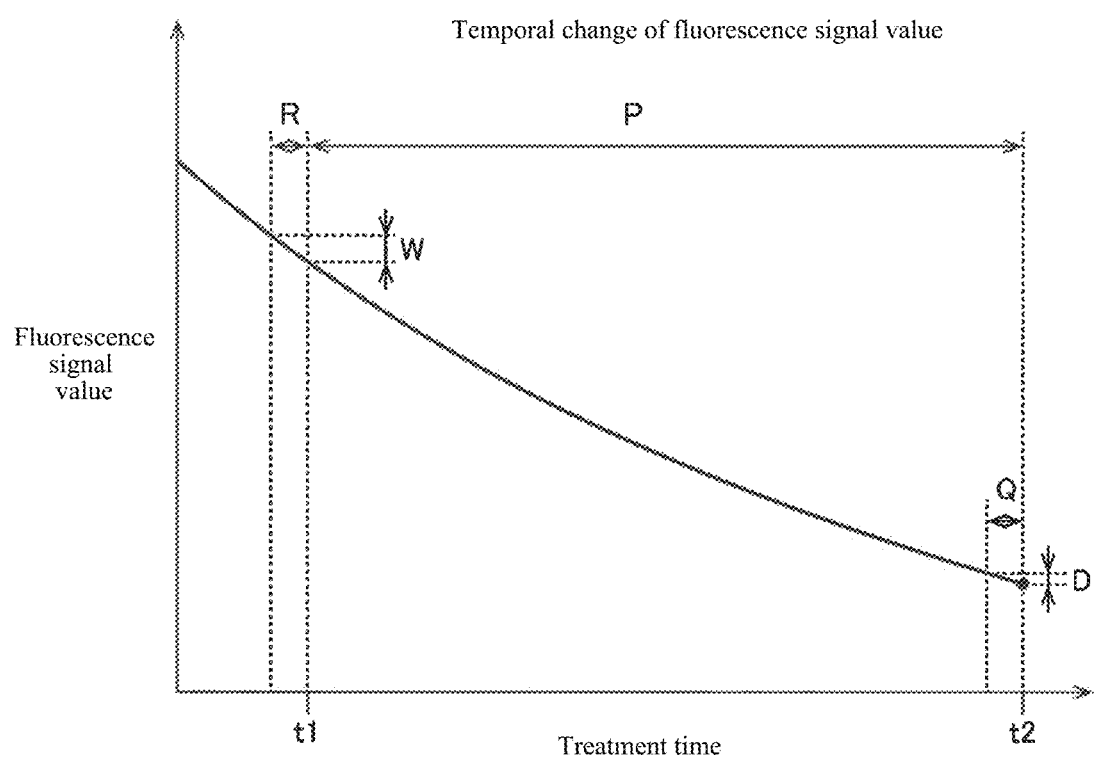
FIG. 7 is a diagram for explaining the calculation of a change rate and a change degree.

In the first embodiment, the change acquisition unit 51 calculates the change rate v1 and the change rate v2, which is the change rate of the fluorescence signal detected by the fluorescence detection unit 23 within the time range R (see FIG. 7). Note that the time range R is an example of the "second time range" recited in claims and the change rate v2 is an example of the "second change rate" recited in claims.

The determination unit 52 determines whether or not the progress of the treatment is in a steady state based on at least the fact that the change degree of the fluorescence signal within the time range Q calculated (acquired) by the change acquisition unit 51 falls within a predetermined range of the change degree.

Specifically, the determination unit 52 determines that the progress of the treatment is in a steady state based on the fact that the change rate v1 falls within the change rate range as a predetermined range of the change degree. In the first embodiment, the determination unit 52 determines that the progress of the treatment is in a steady state based on the fact that the change rate v1 has become near zero. For example, the determination unit 52 determines that the progress of the treatment is in a steady state based on the fact that the change rate v1 has fallen within the zero-neighborhood (0±0.20), which is the change rate range, as described later. The predetermined range of the change degree (change rate range) can be changed by a user, such as, e.g., a doctor.

Further, the determination unit 52 determines whether or not the progress of the treatment is in a steady state based on the comparison between the change rate v1 and the change rate v2. In the first embodiment, the determination unit 52 determines that the progress of the treatment is in a steady state based on that the change rate v1 falls within the change rate range as a predetermined range of the change degree and that the ratio between the change rate v1 and the change rate v2 falls within a predetermined rate ratio range. Specifically, when the change degree X, which is the ratio between the change rate v1 and the change rate v2 (change rate v1/change rate v2), becomes equal to or less than a set threshold, the determination unit 52 determines that the progress of the treatment is in a steady state.

For the change degree X (change rate v1/change rate v2), the threshold to be set is a value near 1. The threshold to be set is, for example, about 0.9 to 0.95. The threshold to be set for the change degree X (change rate v1/change rate v2) can be changed by a user, such as, e.g., a doctor. Further, the determination unit 52 may set the upper limit value and the lower limit value for the change degree X (change rate v1/change rate v2) as a predetermined ratio range for determining that the progress of the treatment is in a steady state.

The operation control unit 53 is configured to control predetermined operations related that the treatment is in a steady state when the determination unit 52 determines that the progress of the treatment is in a steady state.

In a case where it is determined by the determination unit 52 that the progress of the treatment is in a steady state, the predetermined operation to be performed by the control of the operation control unit 53 includes an operation of notifying a user, such as, e.g., a doctor, that the progress of the treatment is in a steady state.

In the first embodiment, it is configured to perform the operation of changing the display method of the display 75 (see FIGS. 8 to 12) indicating the progress of the fluorescence signal by the display unit 70, before and after that the determination unit 52 determines that the progress of the treatment is in a steady state, as the operation of notifying a user, such as, e.g., the doctor, that the progress of the treatment is in a steady state, under control by the operation control unit 53.

Further, in the first embodiment, the treatment support device 100 is configured to perform the operation of stopping the irradiation of the treatment light by the irradiation unit 10 as a predetermined operation under the control of the operation control unit 53 when the determination unit 52 determines that the progress of the treatment is in a steady state. When it is determined by the determination unit 52 that the progress of the treatment is in a steady state, the operation control unit 53 performs the control of stopping the irradiation of the treatment light by the irradiation unit 10 via the control unit 60, as a predetermined operation.

Note that, in the first embodiment, the treatment support device 100 may be configured so as not to perform the operation of stopping the irradiation of the treatment light by the irradiation unit 10 by the change of the setting by the user, such as, e.g., a doctor, when it is determined by the determination unit 52 that the progress of the treatment is in a steady state. That is, it is configured to be switchable between a mode (automatic stop mode) in which the irradiation of the treatment light by the irradiation unit 10 is automatically stopped based on the determination of the determination unit 52 and a mode (manual mode) in which the irradiation of the treatment light by the irradiation unit 10 is stopped by the operation (manipulation) of a user, such as, e.g., a doctor. Note that even in the automatic stop mode, it is possible to stop the irradiation of the treatment light by the irradiation unit 10 by the operation of the user, such as, e.g., a doctor or the like.

Note that the predetermined operation performed under the control of the operation control unit 53 when it is determined that the progress of the treatment is in a steady state is executed, based on the command signal transmitted from the PC 50 (operation control unit 53) when the determination unit 52 determines that the progress of the treatment is in a steady state (a state in which the treatment is considered to have been sufficiently performed).

(Configuration of Control Unit)

The control unit 60 includes a control board (circuit board) on which a CPU, a ROM, a RAM, and the like are mounted. The control unit 60 is configured to control the entire treatment support device 100. The control unit 60 and the PC 50 may be integrally formed.

The control unit 60 is configured to control the irradiation of the treatment light by the irradiation unit 10. The control unit 60 is configured to control turning on and off of the treatment light source 11 (starting the irradiation and stopping the irradiation of the treatment light). The control unit 60 is configured such that a user, such as, e.g., a doctor, can control the start of the irradiation of the treatment light and the stop of the irradiation of the treatment light (switching ON/OFF of the control unit of the treatment light) by operating the operation unit 81 of the control unit 60 or the operation unit 82 of the PC 50.

(Configuration of Display Unit)

The display unit 70 (see FIG. 1) is configured by, for example, a liquid crystal display, or an organic EL (electroluminescent) display. The display unit 70 is connected to the PC 50 and the control unit 60 by, for example, a video interface, such as, e.g., an HDMI.

Figure 2:
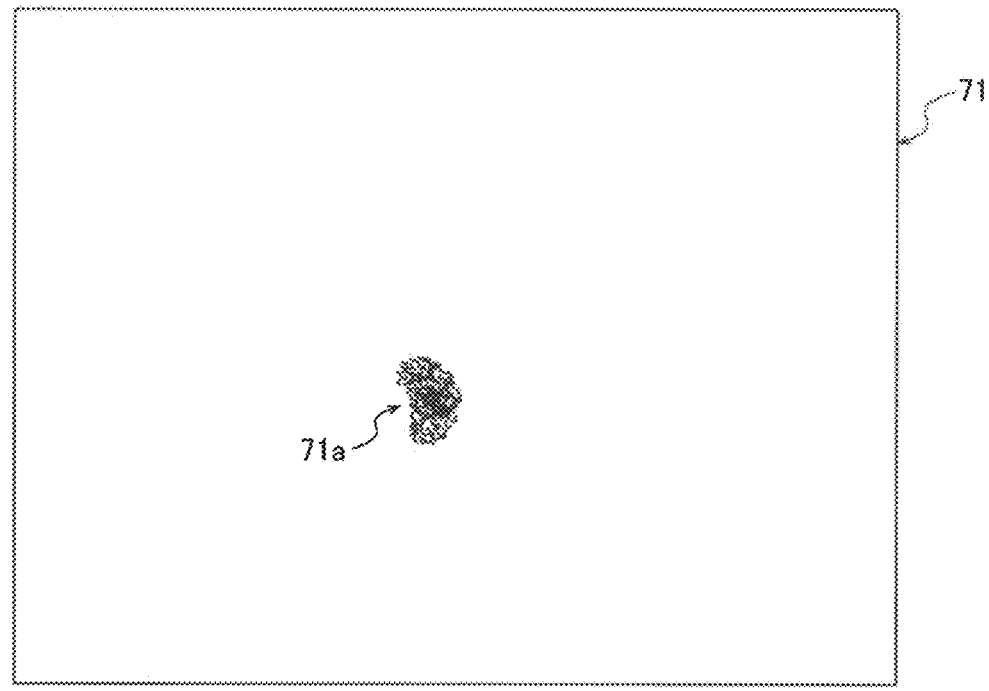
FIG. 2 shows an example of a fluorescence image.

The display unit 70 is configured to display the fluorescence image 71 (see FIG. 2). The fluorescence image 71 is an image showing the distribution status of the fluorescence emitted by the fluorescent material of the medical agent 102. A user, such as, e.g., a doctor, can confirm the integration of the medical agent 102 containing a fluorescent material bound to cancer cells by the distribution 71a of the fluorescence in the fluorescence image 71. The fluorescence image 71 is configured to represent the strength (fluorescence signal value) of the fluorescence from the treatment site by, for example, pixel values (brightness values) of 256 gradations (tones) from 0 to 255. That is, in the fluorescence image 71, the relatively bright (high luminance value) region indicates a region high in the fluorescence intensity, and the relatively dark (low luminance value) region indicates a region low in the fluorescence intensity.

Figure 3:
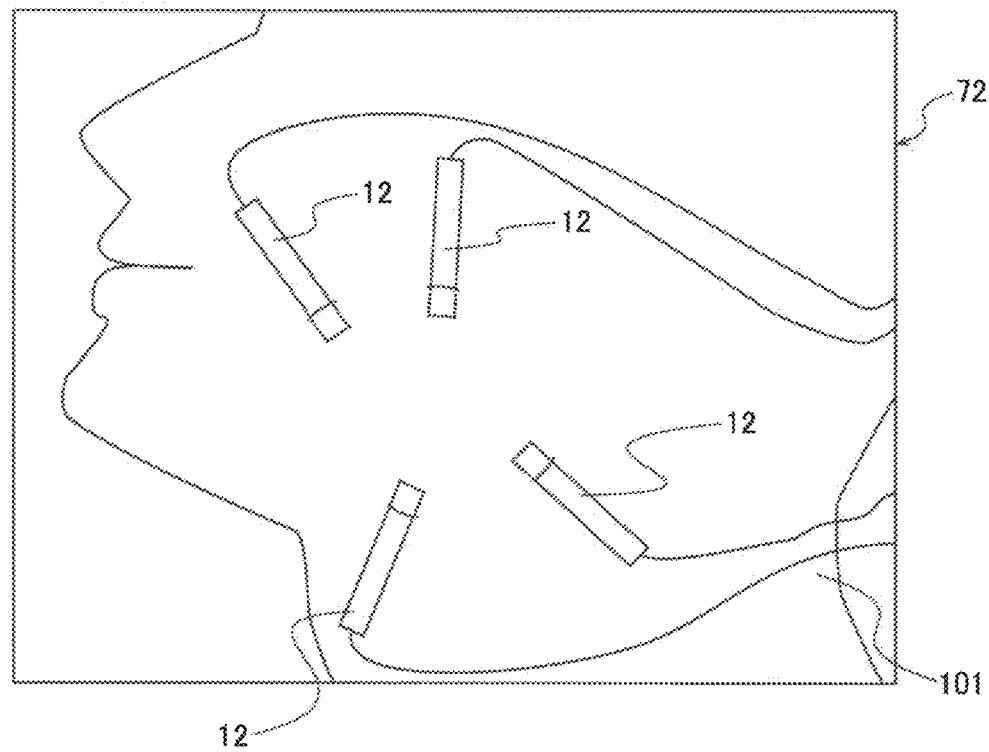
FIG. 3 shows an example of a visible light image.
Figure 4:
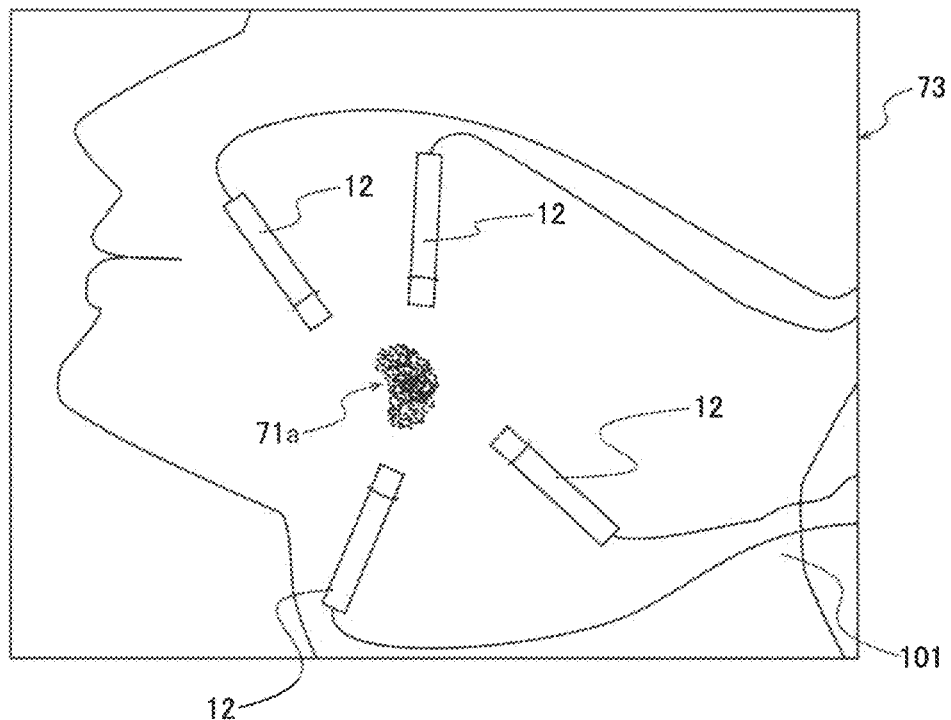
FIG. 4 shows an example of a composite image.
Figure 5:
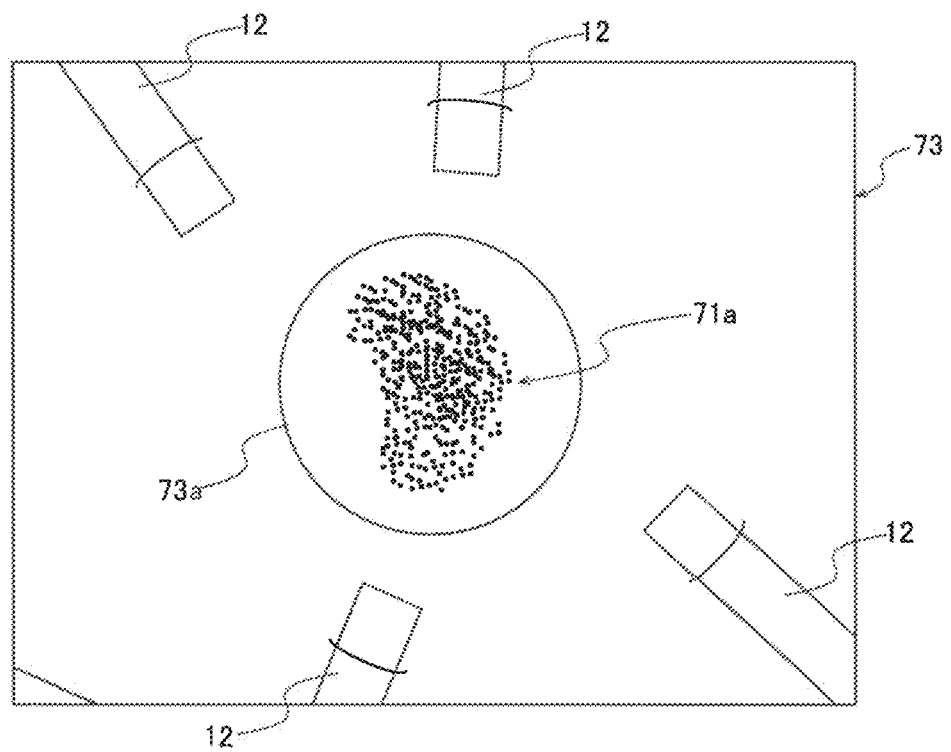
FIG. 5 is a partially enlarged view of FIG. 4.

Further, the display unit 70 is configured to display the visible light image 72 (see FIG. 3). The visible light image 72 is an image based on treatment light and visible light, and reflects, in addition to the visible light, the treatment light leaking out of the body of the cancer patient 101 from the position where the treatment probe 12 is inserted and the treatment light transmitted through the body of the cancer patient 101. A user, such as, e.g., a doctor, can confirm the position of the treatment probe 12 inserted into the cancer patient 101 and the treatment light emitted from the treatment probe 12, by the visible light image 72.

Further, the display unit 70 is configured to be capable of displaying a composite image 73 (see FIGS. 4 and 5) in which the fluorescence image 71 (see FIG. 2) collected by the fluorescence detection unit 23 and the visible light image 72 (see FIG. 3) are superimposed. Thus, a user, such as, e.g., a doctor, can simultaneously confirm the distribution 71a of the fluorescence displayed on the display unit 70, the position of the treatment probe 12, and the position of the treatment light. Note that the composite image 73 is generated by superimposing the image data of the fluorescence image 71 collected by the image collection unit 30 and the image data of the visible light image 72 by the PC 50.

Further, the display unit 70 may simultaneously display the fluorescence image 71 and the visible light image 72 or the composite image 73 side by side. Further, the display unit 70 may selectively display any one of the images of the fluorescence image 71, the visible light image 72, and the composite image 73.

Further, in the first embodiment, the display unit 70 is configured to display the change degree of the fluorescence signal within the time range Q, as described below.

The display unit 70 is configured to display the image 74 (see FIG. 8) showing the temporal change in he fluorescence signal value and the display 75 (see FIG. 8) showing the change degree of the fluorescence signal, as described below. Note that the display 75 (the change rate display 75a, the change rate display 75b, and the change degree display 75c) indicating the image 74 (see FIG. 8) showing the temporal change in the fluorescence signal value and the change degree of the fluorescence signal are an example of the "indication showing the change degree of the fluorescence signal in the display unit" recited in claims.

The display 75 (the change rate display 75a, the change rate display 75b, and the change degree display 75c) indicating the change degree of the fluorescence signal displayed on the display unit 70 is changed in the display manner under the control (command signal from the operation control unit 53) by the operation control unit 53 as an operation of notifying the user, such as, e g., the doctor, that the progress of the treatment is in a steady state, before and after the determination unit 52 determines that the progress of the treatment is in a steady state.

(Configuration of Operation Unit)

The operation units 81 and 82 (see FIG. 1) are user interfaces for operating the treatment support device 100. The operation unit 81, 82 includes, for example, a remote controller, a touch panel, a keyboard, a mouse, and the like. A touch panel as the operation unit 81 or the operation unit 82 may be provided on the display unit 70. That is, the operation unit 81 or the operation unit 82 and the display unit 70 may be integrally configured.

The operation unit 81 is configured to accept operations relating to the control of the treatment support device 100 by the control unit 60. The operations related to the control of the treatment support device 100 by the control unit 60 include operations for starting and stopping irradiation of the treatment light (switching ON/OFF of the irradiation of the treatment light), operations for starting and stopping the detection of fluorescence (collection of fluorescence signal), operations for starting and stopping the detection of the fluorescence, operations for starting and stopping the detection (collection of the signals of the visible light) of the visible light including the treatment light, and the like.

Further, the operation unit 82 is configured to accept the operation to the PC 50 that analyzes visible light signals (data of the fluorescence image 71 and the visible light image 72) including the fluorescence signal and the treatment light. For example, the operation unit 82 is configured to accept the operations for setting the region of interest (Region Of Interest) 73a (see FIG. 5) for selectively acquiring the fluorescence signal. The operation unit 81 may be configured to accept operations for setting the region of interest 73a to selectively acquire a fluorescence signal. At least one of the operation unit 81 and the operation unit 82 is configured to accept an operation (mode setting change operation) for switching between a mode (automatic stop mode) in which the irradiation of the treatment light by the irradiation unit 10 is automatically stopped and a mode (manual stop mode) in which the irradiation of the treatment light by the irradiation unit 10 is stopped by the operation (manual operation) of the user, such as, e.g., a doctor, based on the determination of the determination unit 52.

(Calculation of Change Rate and Change Degree by Change Acquisition Unit)

Next, referring to FIGS. 6 and 7, the calculation of the change rate v1, the change rate v2, and the change degree X by the change acquisition unit 51 will be described.

Figure 6:
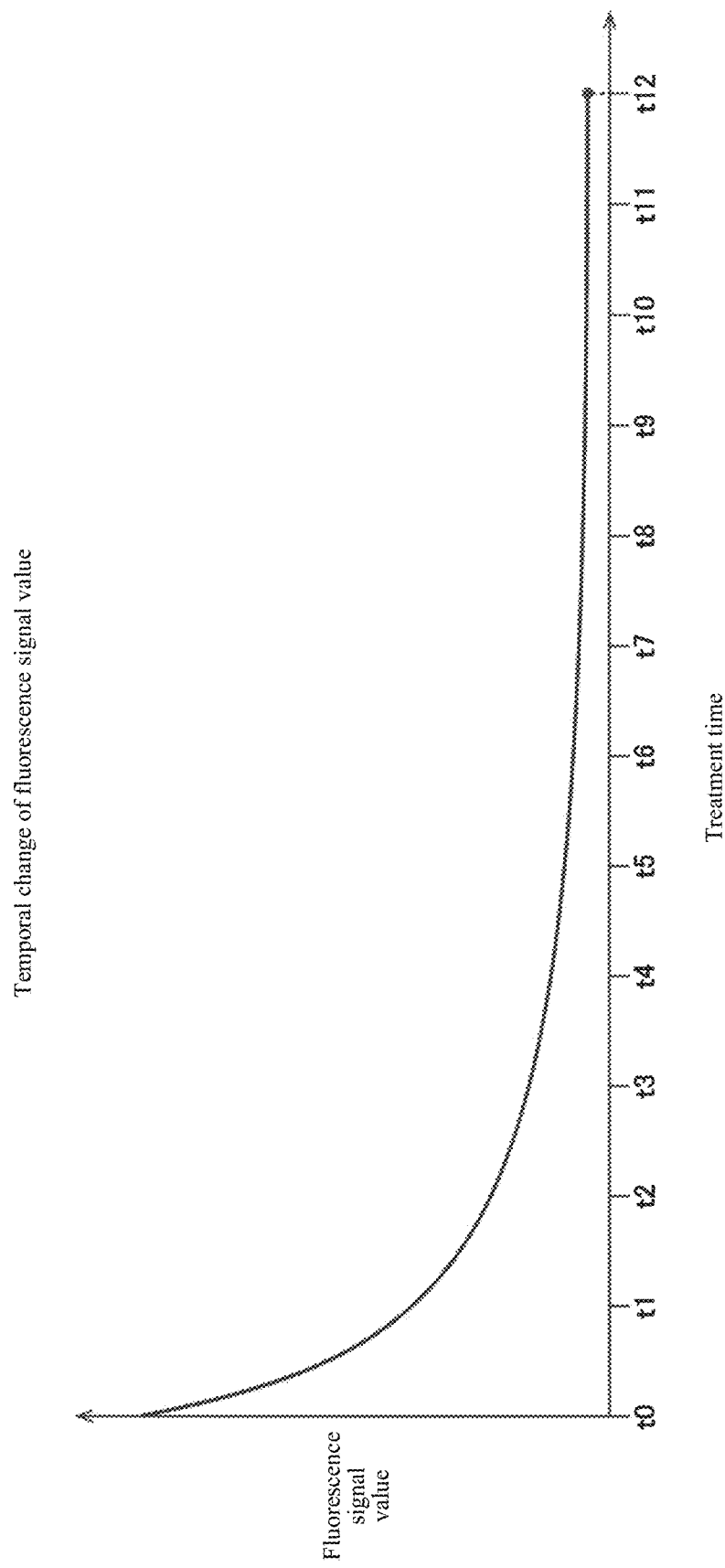
FIG. 6 is a first diagram showing an example of a temporal change in a fluorescence signal value.

In the treatment by photoimmunotherapy, the fluorescence signal value generally temporally changes to draw a decay curve, as shown in FIG. 6. That is, the fluorescence signal value decreases as the treatment time proceeds. In FIG. 6, the vertical axis represents the fluorescence signal value, and the horizontal axis represents the treatment time (irradiation time of the treatment light). FIG. 6 shows the change in the fluorescence signal value at the treatment time t0 to t12.

In the first embodiment, the change acquisition unit 51 calculates the change rate v1 (the displacement D/the time range Q) from the time range Q (see FIG. 7) per the displacement D (see FIG. 7). The time range Q includes the present time within the treatment time. The time range Q is, for example, a time several seconds (1 to 3 seconds) before the present time. As an example, the time range Q at the time t2 is from the time a few seconds (1 to 3 seconds) before the treatment time t2 to the treatment time t2, as shown in FIG. 7. A user, such as, e.g., a doctor, can change the setting of the range (time width) of the time range Q by operating the operation unit 82 or the like.

Further, the change acquisition unit 51 calculates the change rate v2 (the displacement W/the time range R) from the displacement W (see FIG. 7) per the time range R (see FIG. 7).

The time range R includes the time before the time range Q within the treatment time in which the time range Q is included. In the first embodiment, the time range R is a time range that is separate from (not overlapping with) the time range Q in the treatment time in which the time range Q is included. The time range R is, for example, a time range from the time before several seconds (1 to 3 seconds) from the time before the time interval P from the current time to the time before the time interval P from the current time. As an example, the time range R at the time point of the treatment time t2 is, as shown in FIG. 7, a time range from the time a few seconds (1 to 3 seconds) before the treatment time t1, which is a time before the time interval P from the treatment time t2 to the treatment time t1. The time interval P is, for example, about 60 seconds. A user, such as, e.g., a doctor, can change the setting of the range (time width) of the time range R and the range (time width) of the time interval P by operating the operation unit 82 or the like.

(Control By PC and Control Unit)

The change acquisition unit 51 (PC 50) analyzes the change in the fluorescence signal (fluorescence signal value) by acquiring the fluorescence signal value (fluorescence signal strength) collected by the image collection unit 30 for each predetermined time interval. Thus, the change acquisition unit 51 (PC 50) is configured to acquire the change along the time series of the fluorescence signal value. The change acquisition unit 51 (PC 50) of the treatment support device 100 calculates the change in the fluorescence signal value based on the change in the pixel value (brightness value) of 256 gradations from 0 to 255 when the control unit 60 (PC 50) processes the fluorescence signal from 0 to 255 gradations (256 tones) to be displayed on the display unit 70 as the fluorescence image 71. In the first embodiment, the change acquisition unit 51 (PC 50) calculates the change rate v1 and the change rate v2 from the average value of the fluorescence signal values within the set region of interest 73a.

Note that the change acquisition unit 51 (PC 50) may calculate the change rate v1 and the change rate v2 from the average value of the fluorescence signal values (fluorescence signal strength) of the entire region (the entire fluorescence image 71) detected by the fluorescence detection unit 23. Further, the change acquisition unit 51 (PC 50) may calculate each of the change rates v1 and v2 from the maximum value or the minimum value of the fluorescence signal value (fluorescence signal strength) within the region of interest 73a. The change acquisition unit 51 (PC 50) may calculate each of the change rates v1 and v2 from the maxim value or the minimum value of the fluorescence signal value (fluorescence signal strength) in the entire region detected by the fluorescence detection unit 23 (total fluorescence image 71). Furthermore, the fluorescence signal value (fluorescence signal strength) for calculating the change rates v1 and v2 by the change acquisition unit 51 (PC 50) may be a fluorescence signal detected in one region (the region of interest 73a), fluorescence signals detected in a plurality of pixels regions (region of interests 73a), a fluorescence signal detected by one pixel of the image sensor of the fluorescence detection unit 23, or fluorescence signals detected by a plurality of pixels.

Further, as shown in FIGS. 8 to 12, on the display unit 70, an image 74 showing the temporal change in the fluorescence signal value (fluorescence signal strength) detected by the light detection unit 20 (fluorescence detection unit 23) is displayed. In other words, the display unit 70 displays a graph (image 74 showing the temporal change in the fluorescence signal value) showing the change in the fluorescence signal value along the time series (treatment time) at the time of the treatment.

In the first embodiment, the PC 50 is configured to be capable of generating an image to be displayed on the display unit 70 based on at least one of the fluorescence image 71 (see FIG. 2), the visible light image 72 (see FIG. 3), the composite image 73 (see FIG. 4 and FIG. 5), the image 74 (see FIG. 8) showing the temporal change in the fluorescence signal value, and the display 75 (see FIG. 8) showing the change degree of the fluorescence signal. The PC 50 may also be configured to include, as independent hardware, a computer including a processor, such as, e.g., a GPU and an FPGA, as an image composite unit to generate the composite image 73 and generate an image to be displayed on the display unit 70.

Figure 8:
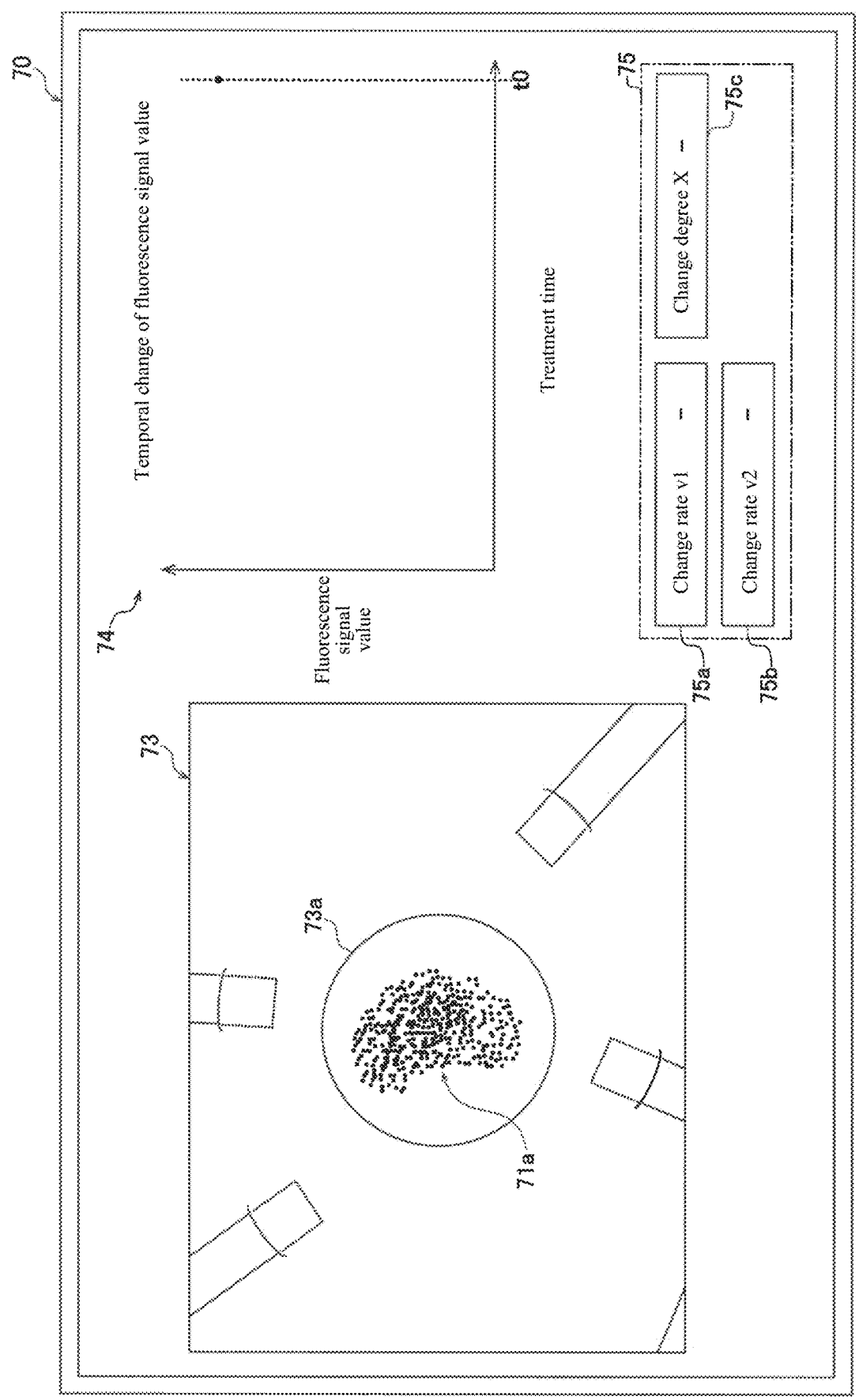
FIG. 8 is a diagram showing an example of a display image displayed at the treatment time t0 in a display unit of a treatment support device according to a first embodiment.

As shown in FIG. 8, the change rate v1, the change rate v2, and the change degree X have not yet be calculated at the treatment time t0 (at the time of starting the treatment). Therefore, in the display 75 (the change rate display 75*a*, the change rate display 75*b*, and the change degree display 75*c*) indicating the change degree in the fluorescence signal in the display unit 70, each of the change rate v1, the change rate v2, and the change degree X are not displayed.

Figure 9:
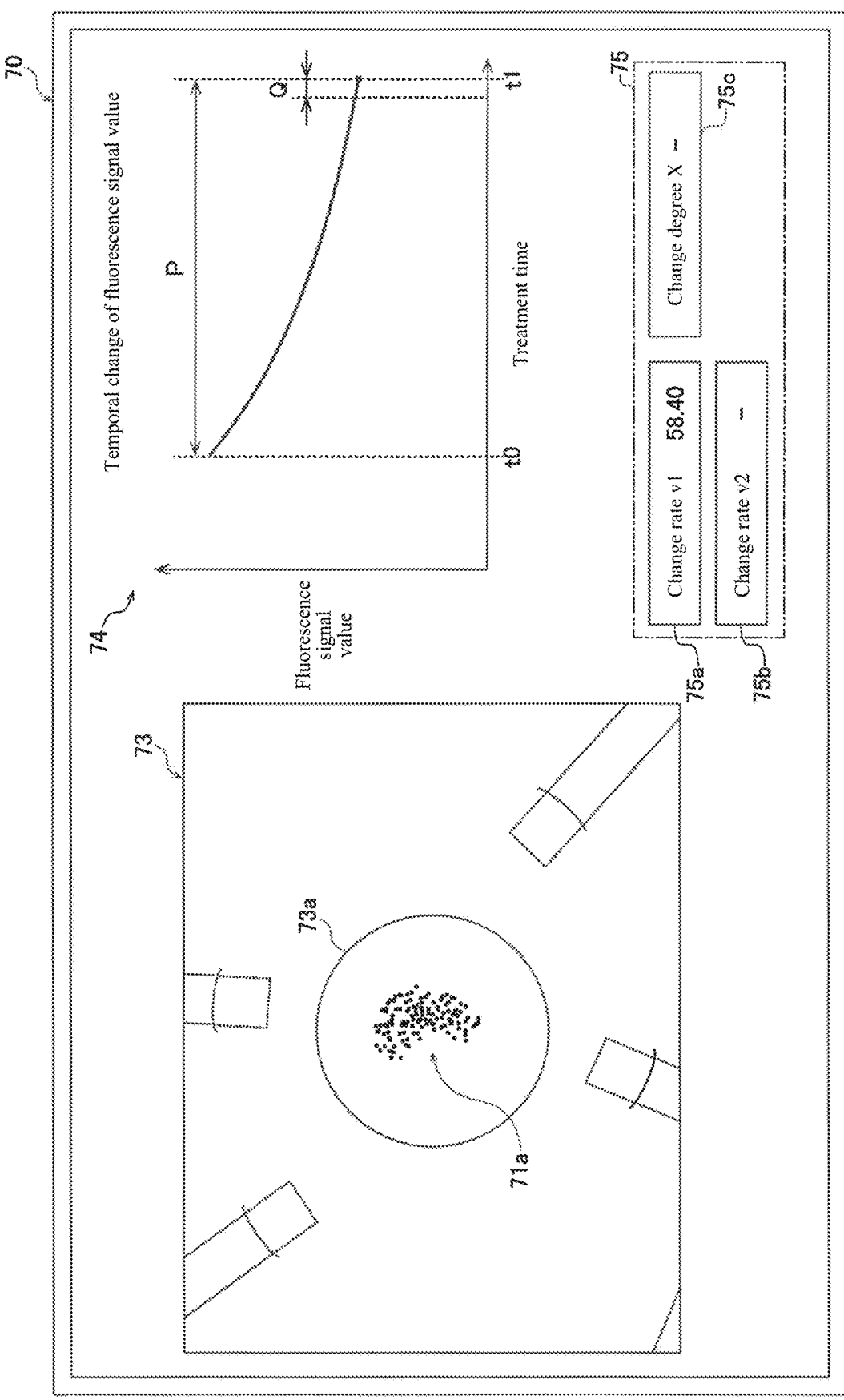
FIG. 9 is a diagram showing an example of a display image displayed at the treatment time t1 in a display unit of a treatment support device according to a first embodiment.

At the treatment time t1, as shown in FIG. 9, the change rate v1 within the time range Q has been calculated by the change acquisition unit 51. Further, since the treatment time t1 is a time point when the time interval P has elapsed from the treatment time t0, the change rate (change rate v2) within the time range R has not yet been calculated. Therefore, in the change rate display 75*a*, the value "58.40" which is the change rate v1 calculated by the change acquisition unit 51 is displayed. But, in the change rate display 75*b* and the change degree display 75*c*, the value of the change rate v2 and the value of the change degree X have not yet been displayed. Note that when only the change rate v1 has been calculated, the value of the change rate v1 may be displayed as the value of the change degree X in the change of degree display 75*c*.

Figure 10:
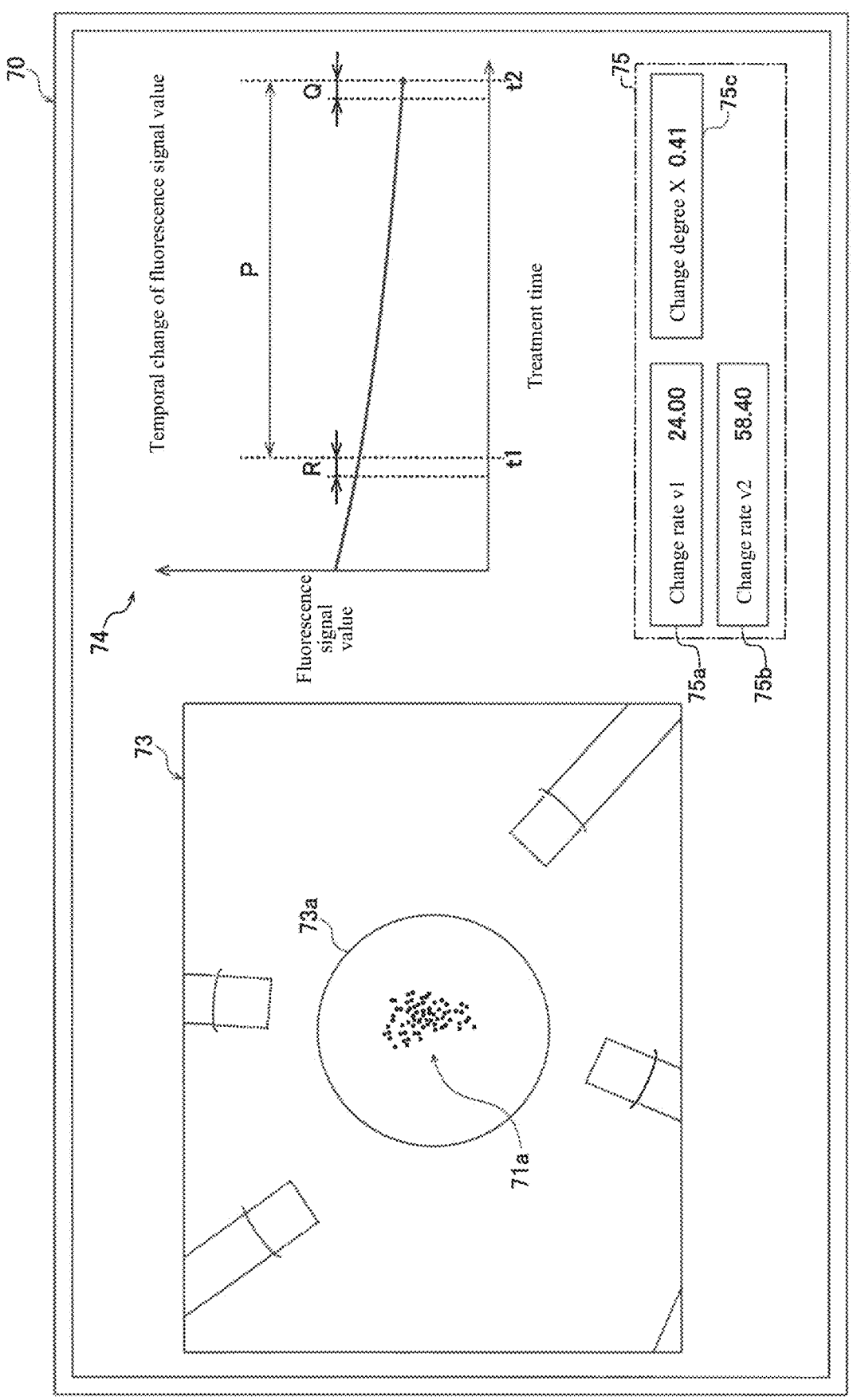
FIG. 10 is a diagram showing an example of a display image displayed at the treatment time t2 in a display unit of a treatment support device according to a first embodiment.

At the treatment time t2, as shown in FIG. 10, the change rate v1 within the time range Q and the change rate v2 within the time range R are calculated by the change acquisition unit 51. As a result, the value "24.00" of the change rate v1 calculated by the change acquisition unit 51 is displayed in the change rate display 75*a*, and the value "58.40" of the change rate v2 is displayed in the change rate display 75*b*. The change acquisition unit 51 calculates the change degree X based on the change rate v1 and the change rate v2. As a result, the value "0.41" of the change degree X calculated by the change acquisition unit 51 is displayed in the change degree display 75*c*.

Figure 11:
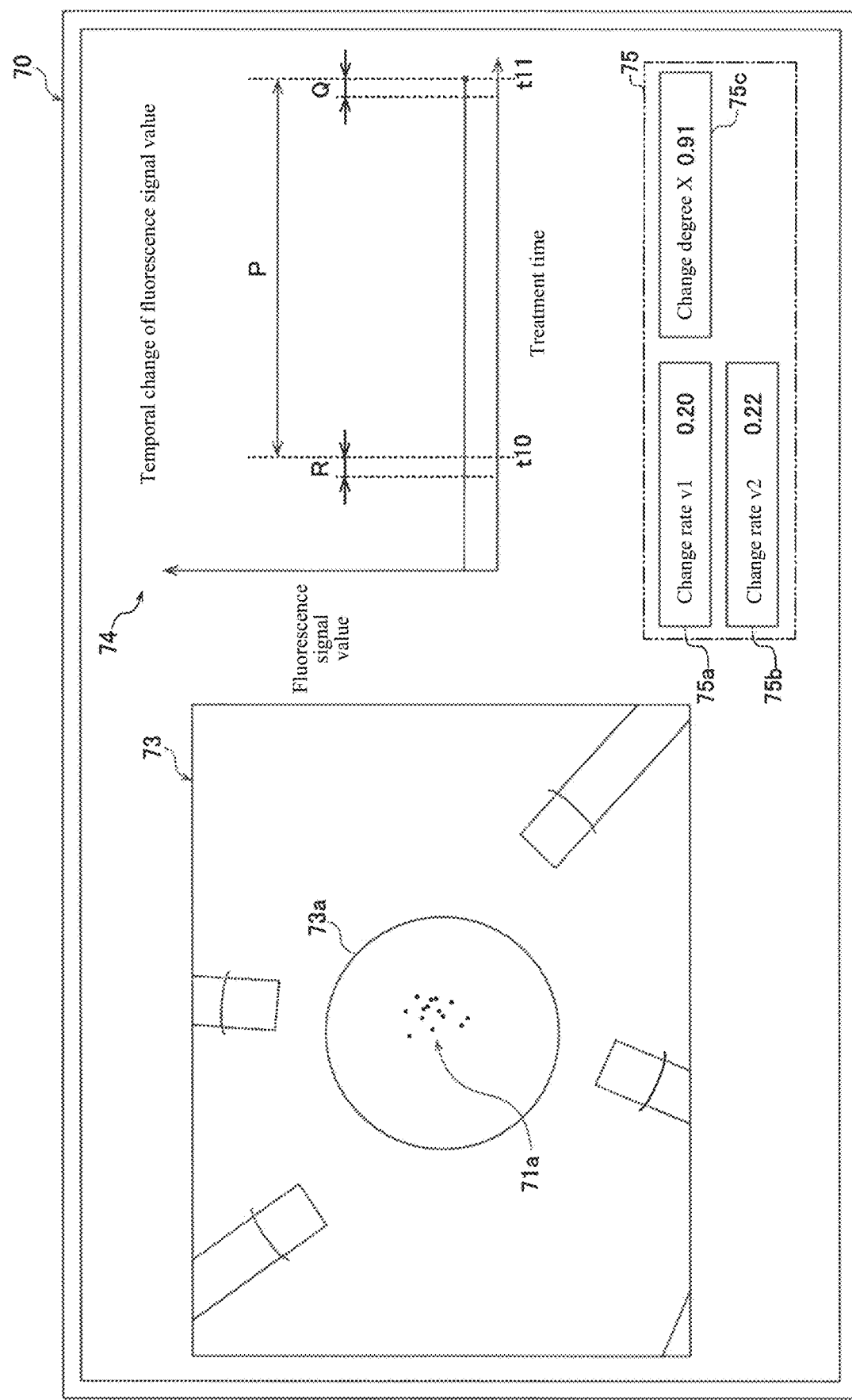
FIG. 11 is a diagram showing an example of a display image displayed at the treatment time t11 in a display unit of a treatment support device according to a first embodiment.

At the treatment time t11, as shown in FIG. 11, the change rate v1 within the time range Q and the change rate v2 within the time range R are calculated by the change acquisition unit 51. With this, the value "0.20" of the change rate v1 calculated by the change acquisition unit 51 is displayed in the change rate display 75*a*, and the value "0.22" of the change rate v2 is displayed in the change rate display 75*b*.

The change acquisition unit 51 calculates the change degree X based on the change rate v1 and the change rate v2. With this, the value "0.91" of the change degree X calculated by the change acquisition unit 51 is displayed in the change degree display 75*c*.

Next, at the treatment time t12, the PC 50 (the determination unit 52) determines that the progress of the treatment is in a steady state (the state in which the treatment is considered to have been sufficiently performed) based on the fact that the change rate v1 falls within the change rate range (near zero) as a predetermined range of the change degree and the ratio of the change rate v1 to the change rate v2 falls within the predetermined rate ratio range (near one). Then, based on the determination result by the PC 50 (determination unit 52), a command signal for controlling a predetermined operation related to the fact that the treatment is in a steady state is transmitted from the operation control unit 53. Then, the PC 50 controls the change (the change of the display image) of the display method of the change rate display 75*a*, the change rate display 75*b*, and the change degree display 75*c*. Further, the control unit 60 receives a command signal transmitted from the operation control unit 53 (PC 50) and controls stopping of the irradiation of the treatment light by the irradiation unit 10.

Note that in a case where the mode has been switched to the mode (manual stop mode) in which the irradiation of the treatment light is stopped by the irradiation unit 10 by a user (manual) of the doctor or the like by the setting change by the user of the doctor or the like, the control of stopping the irradiation of the treatment light by the irradiation unit 10 is not performed by the operation control unit 53 (PC 50), and only the control of changing the display method (changing the display image) of the display 75 (the change rate display 75*a*, the change rate display 75*b*, and the change degree display 75*c*) indicating the change degree of the fluorescence signal is performed.

Figure 12:
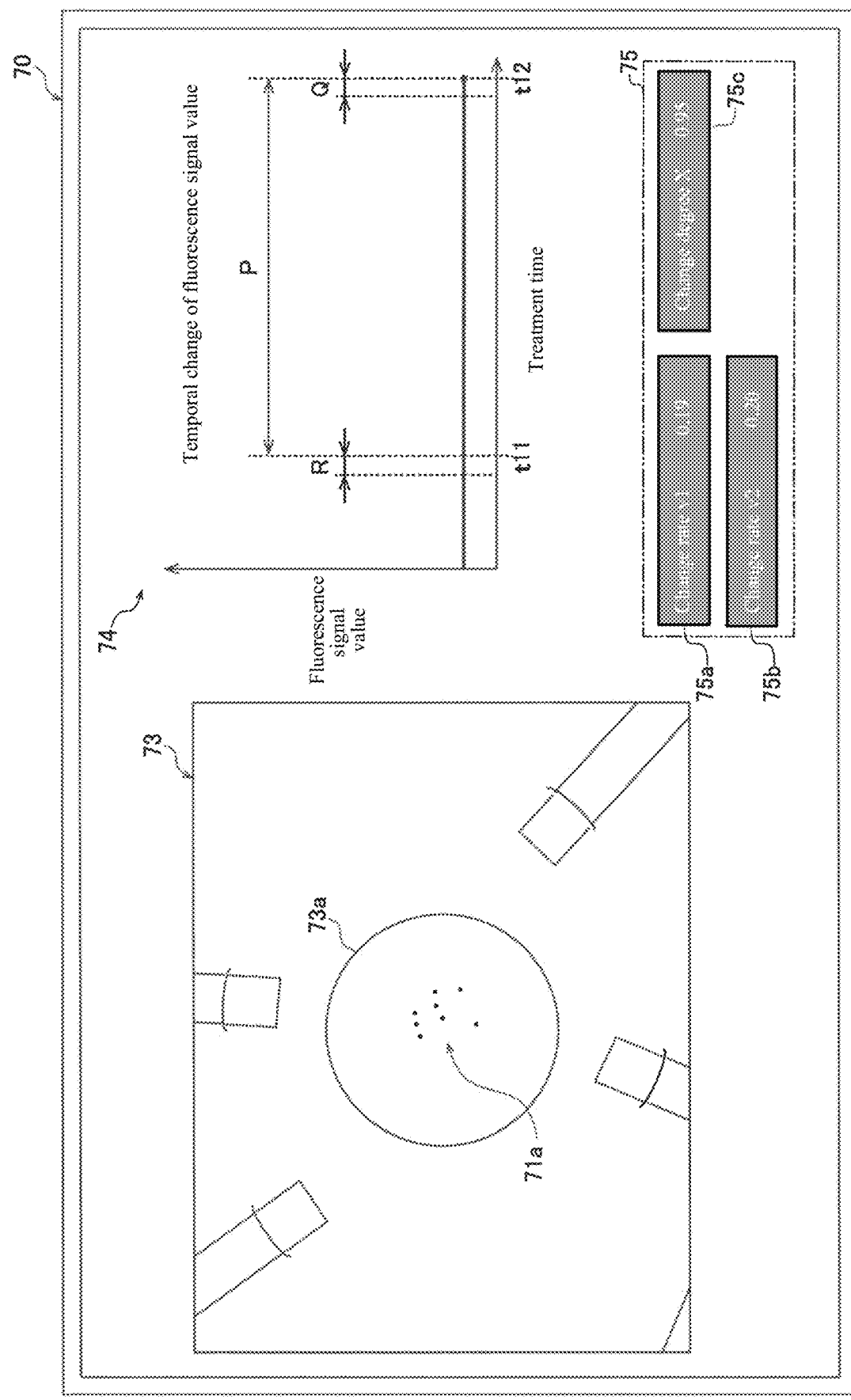
FIG. 12 is a diagram showing an example of a display image displayed in the treatment time t12 in the display unit of the treatment support device according to a first embodiment.

Specifically, at the treatment time t12, as shown in FIG. 12, the value "0.19" of the change rate v1 calculated by the change acquisition unit 51 is displayed in the change rate display 75*a*, and based on the control of the operation control unit 53 (command signal from the operation control unit 53), the display (display image) of the change rate display 75*a* is changed. In the first embodiment, as shown in FIG. 12, the character color and the background color of the change rate display 75*a* are changed from the display before the determination by the determination unit 52 that the progress of the treatment is in a steady state (see FIG. 11).

Further, at the treatment time t12, as shown in FIG. 12, the value "0.20" of the change rate v2 calculated by the change acquisition unit 51 is displayed in the change rate display 75*b*, and the display of the change rate display 75*b* (display image) is changed based on the control of the operation control unit 53 (command signal from the operation control unit 53). In the first embodiment, as shown in FIG. 12, the character color of the change rate display 75*b* and the background color of the change rate display 75*b* have been changed from the indication (see FIG. 11) before the determination unit 52 determines that the progress of the treatment is in a steady state.

Further, in the first embodiment, as shown in FIG. 12, the value "0.95" of the change degree X calculated by the change acquisition unit 51 is displayed in the change degree display 75*c*, and the indication of the change degree display 75*c* (display image) is changed based on the control of the operation control unit 53 (command signal from the operation control unit 53). In the first embodiment, as shown in FIG. 12, the character color of the change degree X and the background color of the change degree X have been changed from the indication before the determination unit 52 determines that the progress of the treatment is in a steady state (see FIG. 11).

As described above, in the first embodiment, the change of the indication (change of the display image) of the change rate display 75*a*, the change rate display 75*b*, and the change degree display 75*c* are simultaneously performed when the change rate v1 is within a predetermined change rate (near zero) as a predetermined change degree and the ratio between change rate v1 and display image v2 is within a predetermined rate ratio range (near one). Then, based on the control of the change of the display method and the control of the operation control unit 53 (command signal from the operation control unit 53), the control of stopping the irradiation of the treatment light by the irradiation unit 10 by the control unit 60 is performed.

Note that the indication of the change rate display 75*a*, the change rate display 75*b*, and the change degree display 75*c* may be changed only by changing the character color such that the character color of each value of the change rate v1, the change rate v2, and the change degree X is changed from black to red, or may be changed only by changing the background color.

Figure 13:
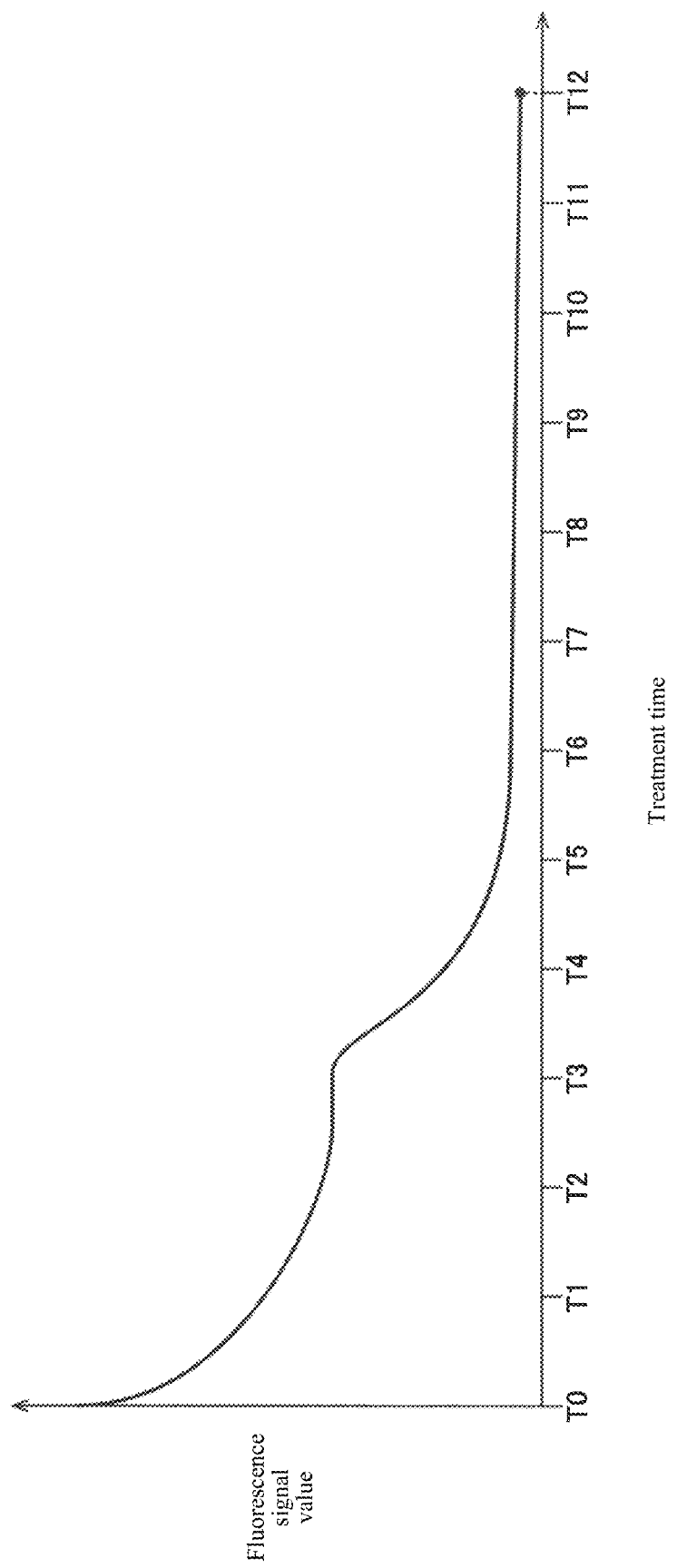
FIG. 13 is a diagram showing another example of a temporal change of a fluorescence signal value.

The temporal change in the fluorescence signal value may change such that, other than the case in which the fluorescence signal value temporarily changes so as to draw a decay curve as shown in FIG. 6, the change in the fluorescence signal value temporarily stagnates (decreases) and then the fluorescence signal value again changes so as to be attenuated as shown in FIG. 13. Note that the vertical axis of FIG. 13 represents the fluorescence signal value, and the horizontal axis represents the treatment time (irradiation time of the treatment light). That is, FIG. 13 is a graph showing the change in the fluorescence signal value at the treatment time T0 to T12.

In such a case, in a case where the progress of the treatment by photoimmunotherapy is determined only by the change (change rate v1) within the time range Q, it may be determined that the treatment progress by photoimmunotherapy has reached the steady state (the state in which it is considered that the treatment has been performed sufficiently) at the time when the time range Q overlaps the section (treatment time T2 to T3 in FIG. 13) in which the change in the fluorescence signal value temporarily stagnates (decreases) in the halfway.

On the other hand, in the first embodiment, the progress of the treatment by photoimmunotherapy is determined by, in addition to the change rate v1, the change degree X (the change rate v1/the change rate v2), which is the ratio between the change rate v1 (the displacement D/the time range Q) within the time range Q and the change rate v2 (the displacement W of the fluorescence signal value/the time range R) within the time range R before the time interval P. As shown in FIG. 13, even in a case where the change rate v1 within the time range Q becomes near zero (see FIG. 14) because the change in the fluorescence signal value temporarily stagnates (decreases) in the middle of the treatment, in a case where the change rate v2 is not the same degree of the change rate (near zero) as the change rate v1, the change degree X does not become 0.95 or less, which is a value in the vicinity of 1.

Figure 14:
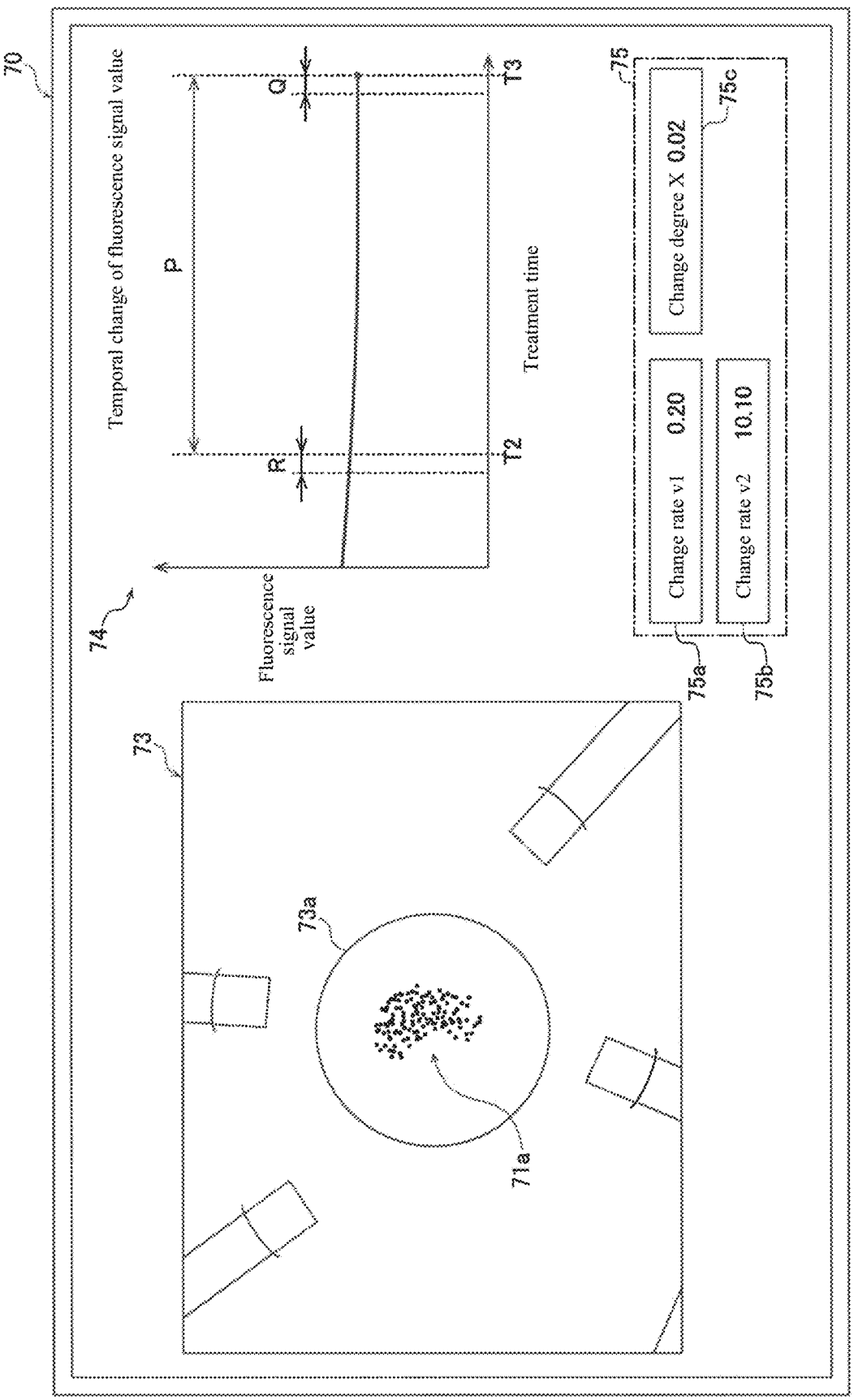
FIG. 14 is a diagram showing an example of a display image displayed at the treatment time T3 in a display unit of a treatment support device according to a first embodiment.

In the first embodiment, even in a case where the progress of the treatment by photoimmunotherapy is temporarily stagnated (reduced), until the change rate V2 becomes the change rate of the same extent as the change rate v1 and the change degree X becomes 0.95 or less which is a value in the vicinity of 1, as shown in FIG. 14, the display method of the display 75 (the change rate display 75*a*, the change rate display 75*b*, and the change degree display 75*c*) indicating the change degree of the fluorescence signal is not changed and the irradiation of the treatment light by the irradiation unit 10 is not stopped. With this, in the first embodiment, it is possible to suppress that the change of the indication method of the display 75 (the change rate display 75*a*, the change rate display 75*b*, and the change degree display 75*c*) indicating the change degree of the fluorescence signal and the stop of the irradiation of the treatment light is performed, as a predetermined progress related that the treatment is in a steady state in a case where it is determined that the progress of the treatment by the determination unit 52 is in a steady state when the progress of the treatment (the change in the fluorescence signal value) by photoimmunotherapy is temporarily stagnated (is small).

Effects of First Embodiment

In this first embodiment, the following effects can be obtained.

In the first embodiment, the treatment support device 100 calculates (acquires) the change degree of the fluorescence signal detected by the fluorescence detection unit 23 within the time range Q (first time range) within the treatment time by the change acquisition unit 51. In a case where the determination unit 52 determines that the progress of the treatment is in a steady state based on the fact that at least the change degree of the fluorescence signal within the time range Q calculated (acquired) by the change acquisition unit 51 falls within a predetermined range of the change degree, the operation control unit 53 controls the predetermined operations related to the treatment being in a steady state.

With this, a user, such as, e.g., a doctor, can recognize that the predetermined operation has been executed by the operation control unit 53 and it has become the state (steady state) which is considered to have been sufficiently performed. As a result, a user, such as, e.g., a doctor, can easily determine the end of the treatment (treatment by photoimmunotherapy) that kills cancer cells based on the irradiation of the treatment light of a predetermined wavelength range to the medical agent 102 containing a fluorescent material administered to the body of the cancer patient 101 (subject).

Further, in the treatment support device 100 according to the above-described first embodiment, the following further effects can be acquired by the following configuration.

Further, in the treatment support device 100 according to the first embodiment, as described above, the change acquisition unit 51 calculates (acquires) the change rate v1 (first change rate), which is a change rate of a fluorescence signal within a time range Q (first time range) detected by the fluorescence detection unit 23, as the change degree of the fluorescence signal. The determination unit 52 determines that the progress of the treatment is in a steady state based on the fact that the change rate v1 has fallen within the range of the change rate.

With this, the determination unit 52 determines that the progress of the treatment is in a steady state based on the fact that the change rate v1 has fallen within the range of the change rate. Therefore, unlike the case in which it is determined that the progress of the treatment is in a steady state based on the fact that the change rate v1 has become a positive (plus) certain threshold or less, it is possible to determine that the progress of the treatment is in a steady state based on the fact that the change rate v1 has fallen within the time range Q between the set upper limit value and lower limit value (the range of the change rate). Therefore, it is possible to suppress that the progress of the treatment is determined to be in a steady state when the change rate v1 is greatly changed in the negative direction because the fluorescence signal value is temporarily increased in the middle of the treatment.

Further, in the treatment support device 100 according to the first embodiment, as described above, the determination unit 52 determines that the progress of the treatment is in a steady state based on the fact that the change rate v1 (first change rate) has become near zero.

With this, the determination unit 52 determines that the progress of the treatment is in a steady state based on the fact that the change rate v1 has become near zero. Therefore, unlike the case in which it is determined that the progress of the treatment is in a steady state based on the fact that the change rate v1 has become a positive (plus) constant threshold or less, it is possible to determine that the progress of the treatment is in a steady state based on the fact that the change rate v1 within the time range Q is reduced in both the plus direction and the minus direction. Therefore, it is possible to further suppress that the progress of the treatment is determined to be in a steady state in a case where the change rate v1 is greatly changed in the negative direction due to the temporary increase in the fluorescence signal value in the middle of treatment.

Further, in the treatment support device 100 according to the first embodiment, as described above, the change acquisition unit 51 calculates (acquires) the change rate v1 (first change rate) and the change rate v2 (second change rate), which is a change rate of the fluorescence signal detected by the fluorescence detection unit 23 within the time range R (second time range) including the time before the time range Q within the treatment time including the change range Q (first time range). Then, the determination unit 52 determines whether or not the progress of the treatment is in a steady state based on the comparison between the change rate v1 and the change rate v2.

As a result, it is determined whether or not the progress of the treatment is in a steady state based on the comparison between the change rate v1 within the time range Q and the change rate v2 within the time range R including the time before the time range Q within the treatment time including the time range Q. Therefore, it is possible to determine whether or not the progress of the treatment is in a steady state based on the comparison between the previous fluorescence signal value change (change rate v2) and the current fluorescence signal value change (change rate v1).

Therefore, the determination unit 52 can determine whether or not the state in which the change of the fluorescence signal value is stagnated (the state in which the change of the fluorescence signal value is small) is continued. As a result, in a case in which the change rate v1 within the time range Q temporarily decreases due to the change of the fluorescence signal value temporarily stagnates (decreases) in the middle of treatment, it is possible to suppress that it is determined that the progress of the treatment is in a steady state.

Further, in the treatment support device 100 according to the first embodiment, as described above, the time range R (second time range) is a time range separated from the time range Q within the treatment time containing the time range Q (first time range).

With this, unlike the case in which the time range R and the time range Q overlap, it is possible to calculate (acquire) a change in the fluorescence signal with a wider time range (longer time range) while suppressing the increase in the data amount for calculating (acquiring) the change rate v1 (first change rate) within the time range Q and the change rate v2 (second change rate) within the time range R. Consequently, the changes in the fluorescence signal with a wider time range (longer treatment time) can be easily calculated (acquired).

Further, in the treatment support device 100 according to the first embodiment, as described above, the determination unit 52 determines that the progress of the treatment is in a steady state based on the fact that the change rate v1 (first change rate) falls within the range of the change rate, and the ratio between the change rate v1 and the change rate v2 (second change rate) falls within a predetermined rate ratio range.

With this, the determination unit 52 determines whether or not the progress of the treatment is in a steady state based on the fact that the ratio between the change rate v1 and the change rate v2 falls within a predetermined rate ratio range in addition to the change rate v1. Therefore, it is possible to determine whether or not the progress of the treatment is in a steady state based on the ratio of the previous change in the fluorescence signal value (change rate v2) and the current change in the fluorescence signal value change (change rate v1). Therefore, the determination unit 52 can easily determine whether or not the state in which the change in the fluorescence signal value is stagnant is being continued. As a result, in a case where the change rate v1 within the time range Q temporarily decreases due to the temporary stagnation of the change of the fluorescence signal value in the middle of treatment, it is possible to further suppress that ii is determined that the progress of the treatment is in a steady state.

Further, in the treatment support device 100 according to the first embodiment, as described above, a predetermined operation to be performed under the control of the operation control unit 53 when it is determined by the determination unit 52 that the progress of the treatment is in a steady state includes the operation of notifying a user, such as, e.g., a doctor, that the progress of the treatment is in a steady state.

With this, since a user, such as, e.g., a doctor, is notified that the progress of the treatment is in a steady state by the predetermined operation performed by the control of the operation control unit 53, a user, such as, e.g., a doctor, can easily recognize by the notification that the condition (steady state) in which the treatment is considered to have been performed sufficiently has reached.

Further, in the treatment support device 100 according to the first embodiment, as described above, the operation of notifying a user, such as, e.g., a doctor, that the progress of the treatment is in a steady state includes the operation of changing the display method of the display indicating the change degree in the fluorescence signal in the display unit 70 before and after the progress of the treatment is determined to be in a steady state by the determination unit 52.

With this, the display method of the display 75 (the change rate display 75a, the change rate display 75b, and the change degree display 75c) indicating the change degree of the fluorescence signal in the display unit 70 before and after it is determined by the determination unit 52 that the progress of the treatment is in a steady state. As a result, a user, such as, e.g., a doctor, can easily recognize that the treatment has reached a steady state by visually recognizing the display 75 indicating the change degree of the fluorescence signal on the display unit 70.

Further, in the treatment support device 100 according to the first embodiment, as described above, the predetermined operation to be performed under the control of operation control unit 53 when it is determined by the determination unit 52 that the progress of the treatment is in a steady state includes the operation of stopping the irradiation of the treatment light by the irradiation unit 10.

As a result, in a case where it is determined by the determination unit 52 that the progress of the treatment is in a steady state, the irradiation of the treatment light by the irradiation unit 10 is stopped by the control of the operation control unit 53. Therefore, when the progress of the treatment has reached the status (steady state) in which the treatment is considered to have been sufficiently performed, the irradiation of the treatment light is automatically stopped, and the treatment can be terminated.

Further, in the treatment support device 100 according to the first embodiment, as described above, a PC 50 (analysis unit) configured to analyze the fluorescence signal detected by the fluorescence detection unit 23 and the control unit 60 configured to control the irradiation of the treatment light by the irradiation unit 10 are provided. The PC 50 includes the change acquisition unit 51, the determination unit 52, and the operation control unit 53. Further, when it is determined by the determination unit 52 that the progress of the treatment is in a steady state, the operation control unit 53 performs control to stop the irradiation of the treatment light by the irradiation unit 10 via the control unit 60 as predetermined operation. With this, it is possible to suppress the complexity of the control unit 60 as compared with the case where the control unit 60 includes the operation control unit 53.

Second Embodiment

Figure 15:
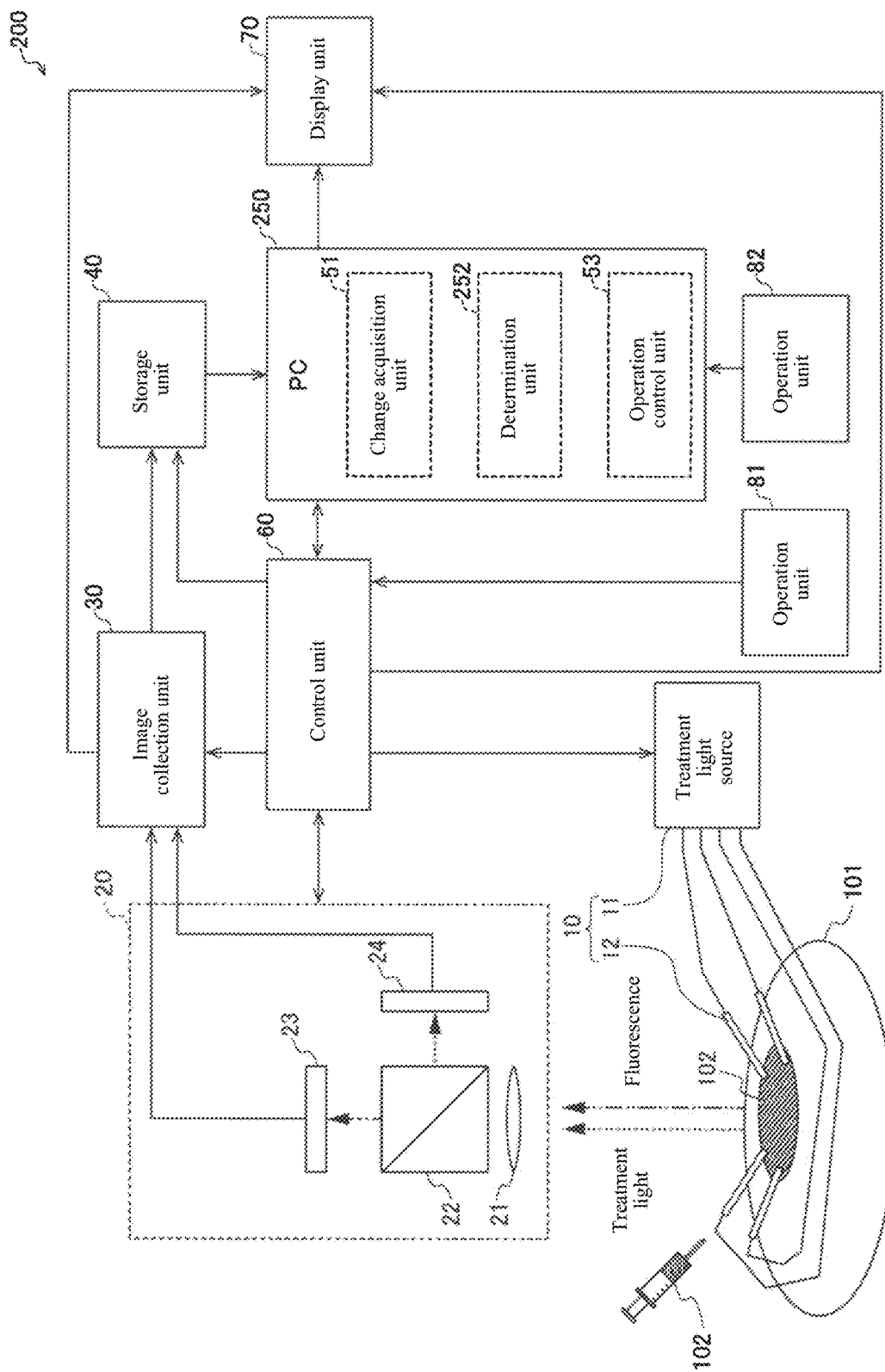
FIG. 15 is a block diagram showing an overall configuration of a treatment support device according to a second embodiment of the present invention.
Figure 16:
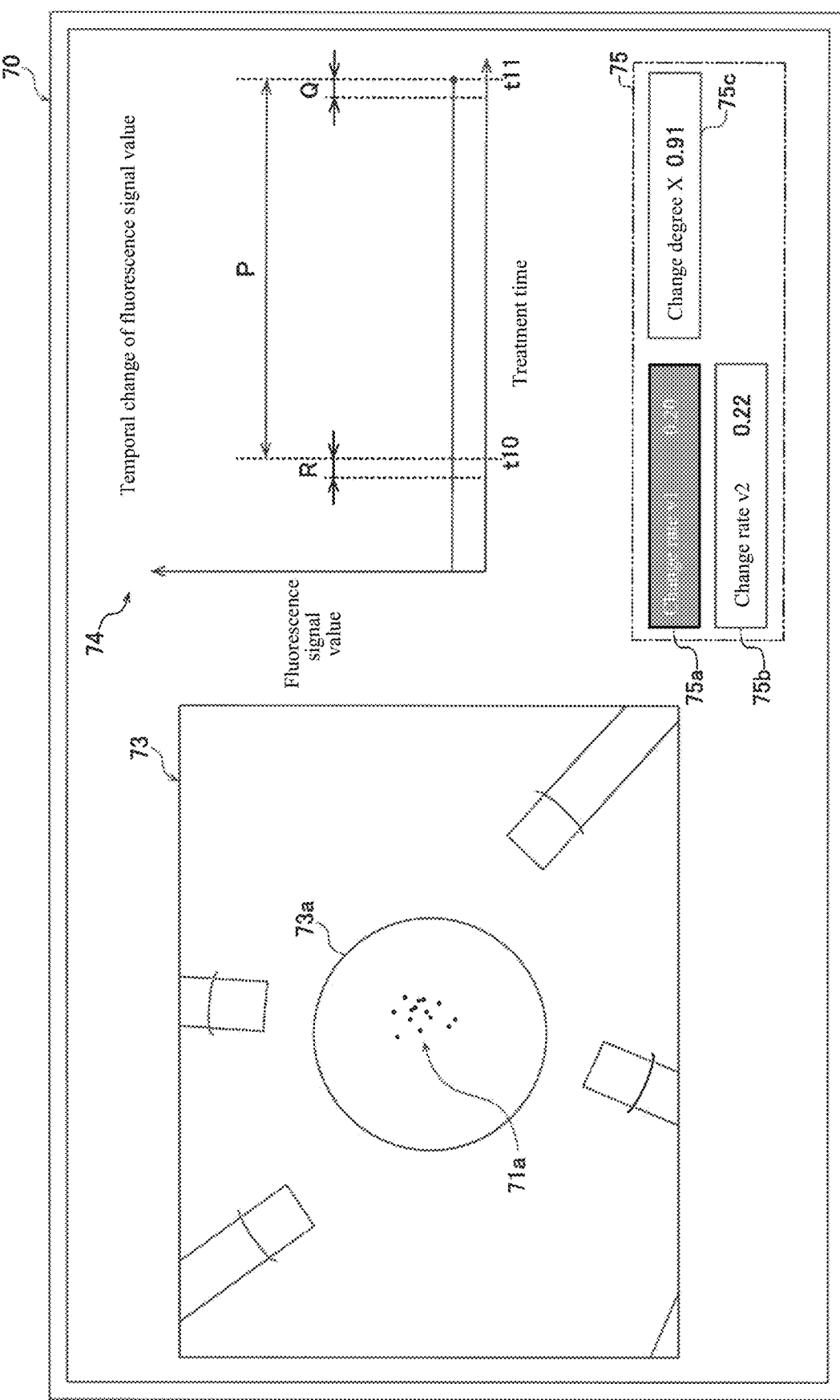
FIG. 16 is a diagram showing an example of a display image displayed at a treatment time t11 in a display unit of a treatment support device according to a second embodiment.

Referring to FIGS. 15 and 16, a configuration of a treatment support device 200 (see FIG. 15) according to a second embodiment will be described. Unlike the first embodiment in which the determination unit 52 determines whether or not the progress of the treatment is in a steady state, based on the fact that the change rate v1 falls within the range (near zero) of the change rate as a predetermined range of the change degree and the ratio between the change rate v1 and the change rate v2 falls within a predetermined rate ratio range, in the second embodiment, the determination unit 252 (see FIG. 15) determines whether or not the treatment progress is in a steady state based on the change rate v1, not based on the ratio (comparison) between the change rate v1 and the change rate v2. Note that the same component as that of the first embodiment is denoted by the same reference symbol, and the description thereof will be omitted.

In the treatment support device 200 according to the second embodiment, the PC 250 includes, as functional components, a change acquisition unit 51, a determination unit 252, and an operation control unit 53. That is, the PC 250 functions as the change acquisition unit 51, the determination unit 252, and the operation control unit 53 by executing programs. Further, the change acquisition unit 51, the determination unit 252, and the operation control unit 53 are functional blocks as software in the PC 250, and are configured to function based on a command signal of the PC 250 as hardware.

The determination unit 252 determines that the progress of the treatment is in a steady state, based on the fact that the change rate v1 falls within the change rate range as a predetermined range of the change degree. In the second embodiment, the determination unit 252 determines that the progress of the treatment is in a steady state, based on the fact that the change rate v1 has reached near zero. For example, the determination unit 252 determines that the progress of the treatment is in a steady state based on the fact that the change rate v1 has fallen within the zero-neighborhood (0±0.20), which is a change rate range. The predetermined range of the change degree (change rate range) can be changed by a user, such as, e.g., a doctor.

In the treatment support device 100 according to the second embodiment, at the treatment time t11, the determination unit 252 (PC 250) determines that the progress of the treatment is in a steady state (a state in which the treatment is considered to have been fully performed), based on the fact that the change rate v1 has fallen within the change rate range (near zero) as a predetermined range of the change degree. Based on the determination result by the determination unit 252 (PC 250), a command signal for controlling the predetermined operation related to the fact that the treatment is in a steady state is transmitted from the operation control unit 53.

The PC 250 controls the change of the display method of the change rate display 75a, based on the command signal of the operation control unit 53. Further, the control unit 60 receives the command signal transmitted from the operation control unit 53 (PC 250) and controls stopping the irradiation of the treatment light by the irradiation unit 10. In a case where the mode is switched to the mode (manual stop mode) in which the irradiation of the treatment light is stopped by the irradiation unit 10 by a user (manual), such as, e.g., a doctor, by the setting change by a user, such as, e.g., a doctor, in the same manner as in the first embodiment, the control to stop the irradiation of the treatment light is not performed, and only the control of changing the display method (change in the display image) of the change rate display 75a is performed.

At the treatment time t11, as shown in FIG. 16, the change rate v1 calculated by the change acquisition unit 51 has fallen within the range of near zero (0±0.20) is displayed on the change rate display 75a, and the value "0.20" of the change rate v1 calculated by the change acquisition unit 51 is displayed in the change rate display 75a, and the display of the change rate display 75a is changed based on the control (command signal from the operation control unit 53) of the operation control unit 53. In the second embodiment, as shown in FIG. 16, the character color and the background color of the change rate display 75a are changed from the display (see FIG. 10) before falling within the range of near zero (0±0.20).

The change of the display of the change rate display 75a may be changed, for example, by changing only the character color of the value of the change rate v1, for example, from black to red, or by changing only the background color. Then, together with the control of the change of the display method, based on the control of the operation control unit 53 (command signal from the operation control unit 53), the control of stopping the irradiation of the treatment light by the irradiation unit 10 is performed.

The rest of the configuration of the second embodiment is the same as that of the first embodiment.

Effects of Second Embodiment

In the second embodiment, in the same manner as in the above-described first embodiment, a user, such as, e.g., a doctor, can easily determine the end of the treatment (treatment by photoimmunotherapy) for killing cancer cells based on irradiation of treatment light in a predetermined wavelength range to the medical agent 102 containing a fluorescent material administered to the body of a cancer patient 101 (subject).

Modified Embodiment

It should be understood that the embodiments disclosed here are examples in all respects and are not restrictive. The scope of the present invention is shown by claims rather than the descriptions of the embodiments described above, and includes all changes (modifications) within the meaning of equivalent to the claims.

For example, in the first and second embodiments, an example is shown in which the change acquisition unit 51 calculates (acquires) the change rate v1 (first change rate), which is a change rate of a fluorescence signal within the time range Q (first time range) detected by the fluorescence detection unit 23, and that the determination unit 52 (determination unit 252) determines that the progress of the treatment by photoimmunotherapy is in a steady state based on the fact that the change rate v1 has fallen within the change rate range, but the present invention is not limited thereto. In the present invention, the change acquisition unit may calculate the acceleration or the displacement of the fluorescence signal within the first time range. In this case, the determination unit determines that the progress of the treatment is in a steady state based on the fact that the accelerations or the displacement value calculated by the change acquisition unit has fallen within the predetermined limit.

Further, in the first and second embodiments, an example is shown in which the change acquisition unit 51 calculates the change rate v1 (first change rate), which is the change rate of the fluorescence signal within the time range Q (first time range) detected by the fluorescence detection unit 23, as the change degree of the fluorescence signal, but the present invention is not limited thereto. In the present invention, the change acquisition unit may acquire the change degree of the fluorescence signal detected by the fluorescence detection unit within the first time range within the treatment time from a graph or a table or the like showing the change in the fluorescence signal detected by the fluorescence detection unit.

In addition, in the first and second embodiments described above, an example is shown in which the determination unit 52 (determination unit 252) determines that the progress of the treatment by photoimmunotherapy is in a steady state, based on the fact that the change rate v1 (first change rate) has become near zero, but the present invention is not limited thereto. In the present invention, the determination unit may determine that the progress of the treatment is in a steady state based on the fact that the first change rate has become below a set threshold.

Further, in the above-described first embodiment, an example is shown in which the determination unit 52 determines whether or not the progress of the change rate is in a steady state, based on the fact that the change rate v1 (first change rate) is within the change rate range and the ratio between the change rate v1 and the change rate v2 (second change rate) is within a predetermined rate ratio range. In the second embodiment, an example is shown in which the determination unit 252 determines whether or not the progress of the treatment is in a steady state based on the change rate v1 rather than based on the ratio (comparison) between the change rate v1 and the change rate v2. However, the present invention is not limited to the above. In the present invention, the determination unit may be switchable between: a mode in which it is determined whether or not the progress of the treatment by photoimmunotherapy is in a steady state based on the fact that the first change rate falls within the change rate range and the ratio between the first change rate and the second change rate falls within a predetermined rate ratio range; and a mode in which it is determined whether or not the progress of the treatment is in a steady state based on the first change rate, rather than based on the ratio between the first change rate and the second change rate.

Further, in the first and second embodiments, an example is shown in which the time range R (second time range) is a time range separated from the time range Q within the treatment time including the time range Q (first time range), but the present invention is not limited thereto. In the present invention, the first time range and the second time range may overlap (partially overlap).

Further, in the above-described first embodiment, an example is shown in which the determination unit 52 determines that the progress of the treatment by photoimmunotherapy is in a steady state based on the fact that the steady state v1 (first change rate) falls within the change rate range and the ratio between the change rate v1 and the change rate v2 (second change rate) falls within the predetermined rate ratio range, but the present invention is not limited thereto. In the present invention, the determination unit may determine that the progress of the treatment is in a steady state based on the fact that the first change rate and the second change rate have fallen within a predetermined change rate range set for each of them.

Further, in the first and second embodiments, an example is shown in which the predetermined operations to be performed by the control of the operation control unit 53 when the determination unit 52 (determination unit 252) determines that the progress of the treatment is in a steady state include an operation of notifying the user that the progress of the treatment by photoimmunotherapy is in a steady state, but the present invention is not limited thereto. In the present invention, the predetermined operation to be performed by the operation control unit control when it is determined by the determination unit that the progress of the treatment is in a steady state may include only the operation of stopping the irradiation of the treatment light by the irradiation unit 10, without including the operation of notifying the user that the progress of the treatment is in a steady state.

Further, in the above-described first and second embodiments, an example is shown in which the operation of notifying a user, such as, e.g., a doctor—that the progress of the treatment is in a steady state includes the operation of changing the display method of the display 75 indicating the change degree of the fluorescence signal in the display unit 70 before and after the determination unit 52 (determination unit 252) determines that the progress of the treatment is in a steady state, but the present invention is not limited thereto. In the present invention, the treatment support device may be provided with a speaker or the like, and the operation of notifying the user that the progress of the treatment is in a steady state may include the operation of notification by voice. That is, a notification other than the visual notification may notify that the progress of the treatment is in a steady state.

In the first and second embodiments, an example is shown in which the predetermined operation to be performed under the control of the operation control unit 53 when determination unit 52 (determination unit 252) determines that the progress of the treatment is in a steady state includes the operation of stopping the irradiation of the treatment light by irradiation unit 10, but the present invention is not limited thereto. In the present invention, the predetermined operation to be performed by the operation control unit control when it is determined by the determination unit that the treatment progress is in a steady state may not include the operation of stopping the irradiation of the treatment light by the irradiation unit, but may include only the operation of notifying the user that the progress of the treatment by photoimmunotherapy is in a steady state.

Further, in the first and second embodiments, an example is shown in which the PC 50 or 250 (analysis unit) includes a change acquisition unit 51, a determination unit 52 (determination unit 252), and an operation control unit 53 as functional configurations (software-based configurations), but the present invention is not limited thereto. For example, each of the change acquisition unit, the determination unit, and the operation control unit may be configured as separate hardware (arithmetic circuits) separate from the hardware (arithmetic circuits) of the analysis unit.

Figure 17:
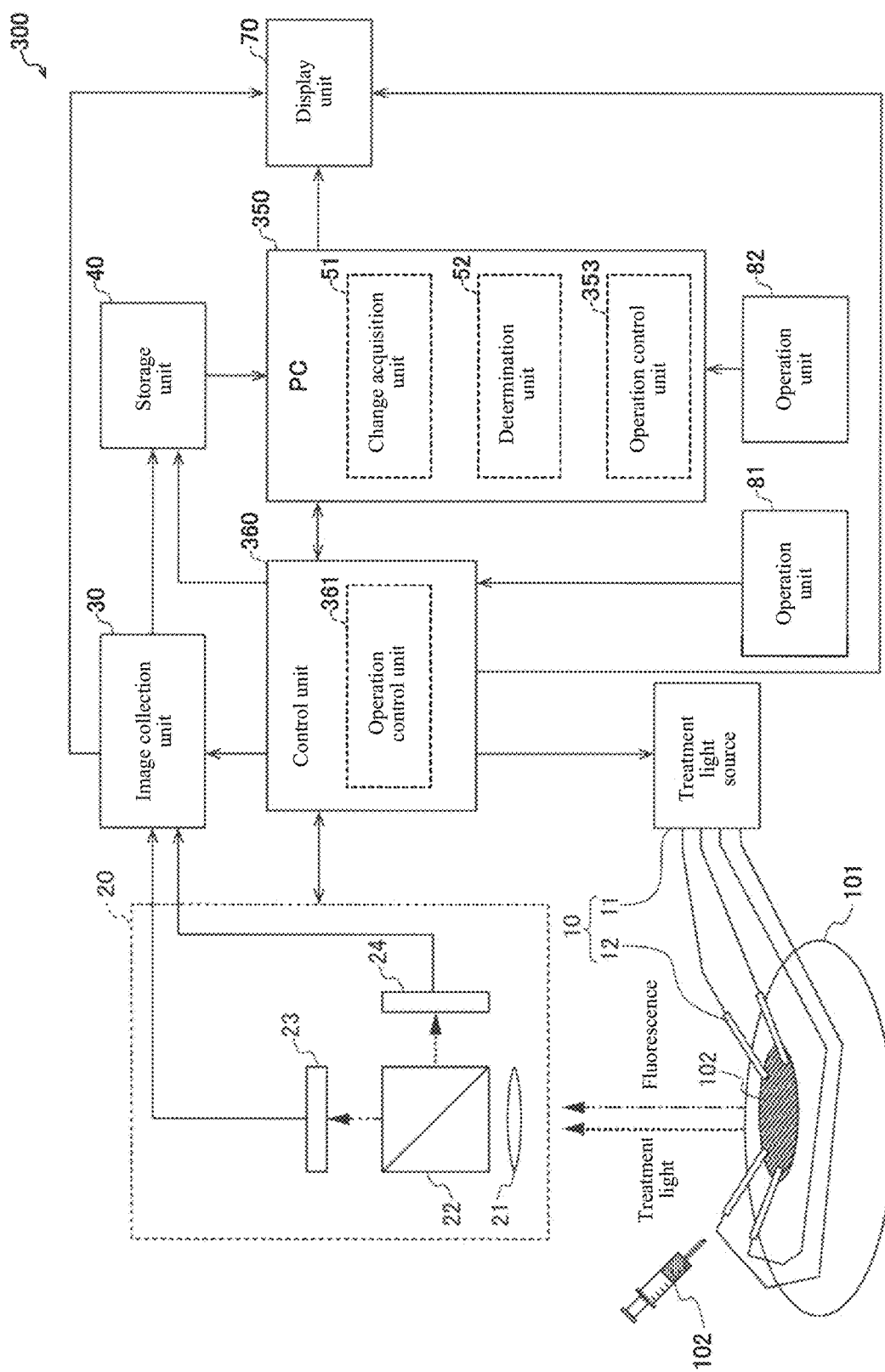
FIG. 17 is a block diagram showing an overall configuration of a treatment support device according to a first modification of the present invention.

In the first and second embodiments, an example is shown in which the PC 50 or 250 (analysis unit) as hardware includes the operation control unit 53 as a functional configuration (software-like configuration), but the present invention is not limited thereto. For example, the operation control unit may be provided on each of the analysis unit and the control unit. For example, as in the treatment support device 300 according to the first modification shown in FIG. 17, the PC 350 (analysis unit) may be provided with an operation control unit 353 for controlling the operation of changing the display method of the indication indicating the change degree of the fluorescence signal in the display unit 70, and the control unit 360 may be provided with an operation control unit 361 for controlling the operation of stopping the irradiation of the treatment light by the irradiation unit 10.

In the above-mentioned first and second embodiments, an example is shown in which the PC 50 or 250 (analysis unit) as hardware includes the change acquisition unit 51, the determination unit 52 (determination unit 252), and the operation control unit 53 as a functional configuration (software-like configuration), but the present invention is not limited thereto. For example, the analysis unit and the control unit may be integrally configured as the same hardware (arithmetic circuits), and the integrally configured analysis unit and the control unit may include the change acquisition unit, the determination unit, and the operation control unit as a functional configuration (software-based configuration).

Figure 18:
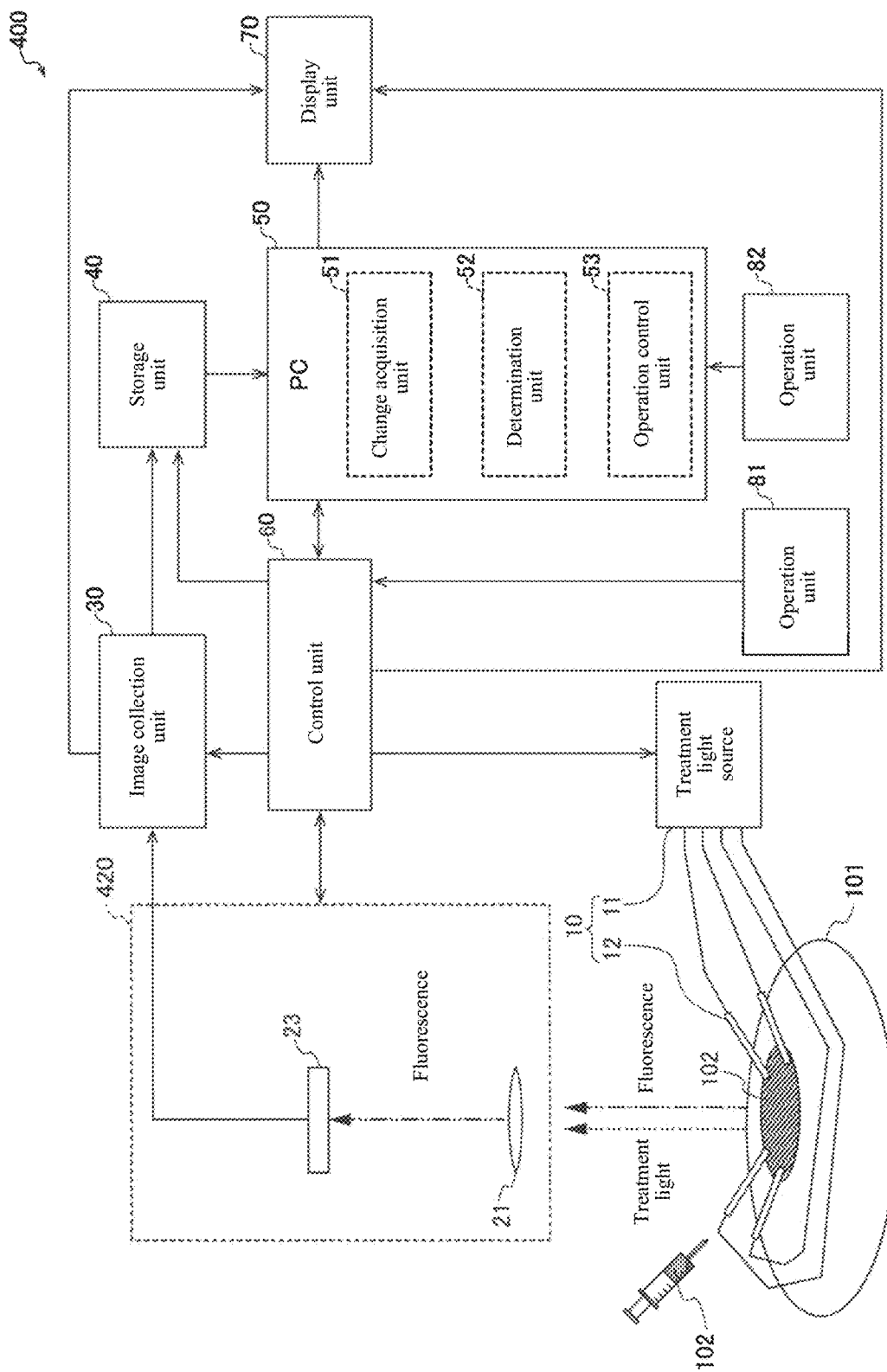
FIG. 18 is a block diagram showing an overall configuration of a treatment support device according to a second modification of the present invention.

Further, in the first and second embodiments, an example is shown in which the light detection unit 20 includes the fluorescence detection unit 23 and the treatment light detection unit 24, but the present invention is not limited thereto. In the present invention, as in the treatment support device 400 according to the second modification shown in FIG. 18, the light detection unit 420 may be configured to include only the fluorescence detection unit 23. As a result, the device configuration of the treatment support device 400 (light detection unit 420) can be simplified.

Figure 19:
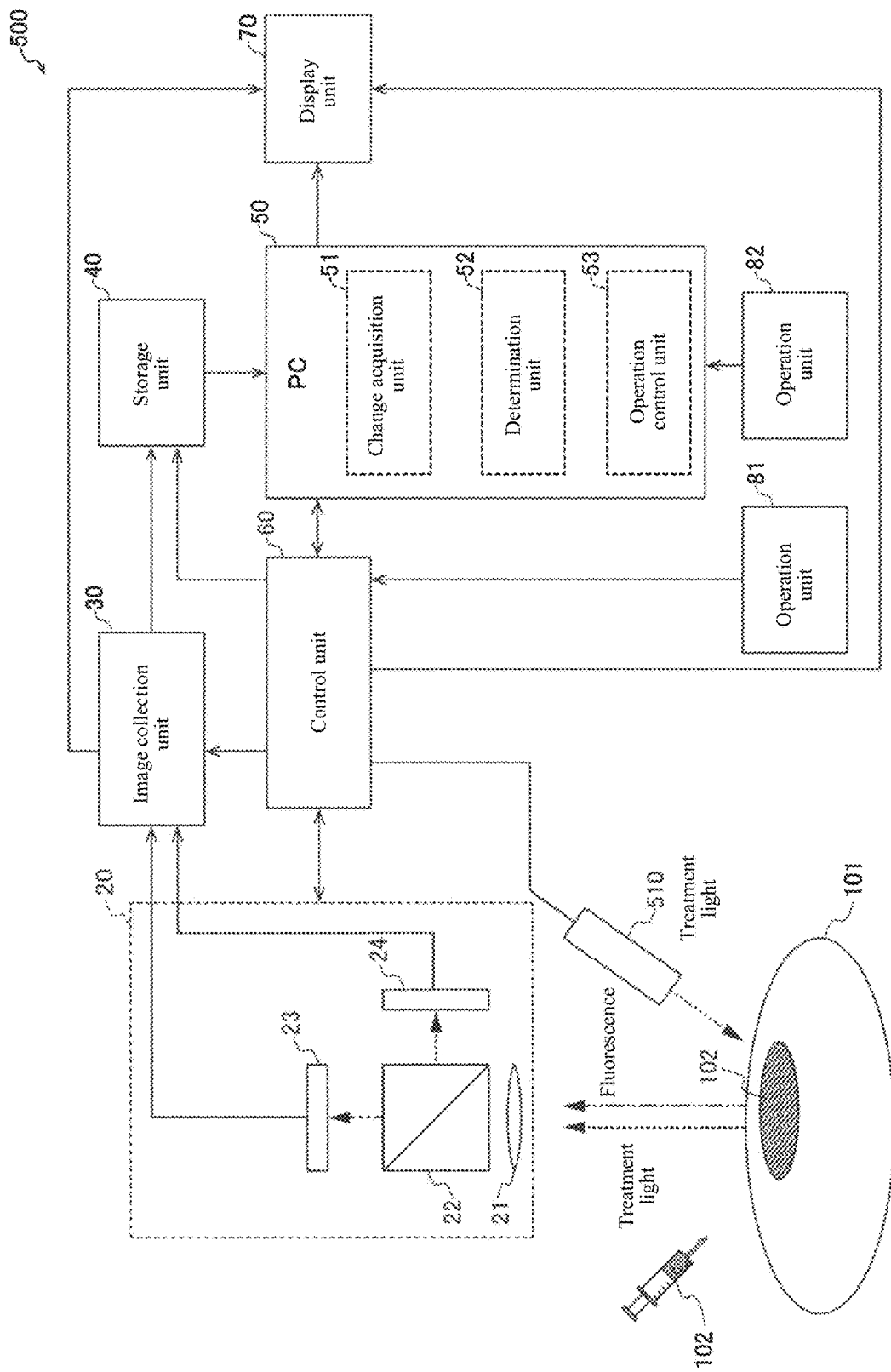
FIG. 19 is a block diagram showing an overall configuration of a treatment support device according to a third modification of the present invention.

Further, in the first and second embodiments described above, an example has been described in which the irradiation unit 10 (treatment probe 12) performs the irradiation of the treatment light in the body of the cancer patient 101, but the present invention is not limited thereto. In the present invention, as in the treatment support device 500 according to the third modification shown in FIG. 19, it may be configured to perform the irradiation of the treatment light from outside the body of the cancer patient 101 by the irradiation unit 510. Note that the irradiation unit 510 includes a light source, such as, e.g., a semiconductor laser (LD: Laser Diode) and a light emitting diode (LED: Light Emitting Diode).

[Aspects]

It will be understood by those skilled in the art that the above-described embodiments are concrete examples of the following aspects.

(Item 1)

A treatment support device comprising:
- an irradiation unit configured to irradiate a medical agent with treatment light in treatment for killing cancer cells by irradiating the medical agent with the treatment light of a predetermined wavelength, the medical agent including a fluorescent material administered to a body of a subject;
- a fluorescence detection unit configured to detect fluorescence emitted by the fluorescent material of the medical agent excited by irradiation of the treatment light;
- a change acquisition unit configured to acquire a change degree of a fluorescence signal detected by the fluorescence detection unit in a first time range within a treatment time;
- a determination unit configured to determine whether or not a progress of the treatment is in a steady state, based on at least a fact that the change degree of the fluorescence signal within the first time range acquired by the change acquisition unit has fallen within a predetermined range of the change degree; and
- an operation control unit configured to control a predetermined operation related to a fact that the treatment is in the steady state when it is determined by the determination unit that the progress of the treatment is in the steady state.

(Item 2)

The treatment support device as recited in the above-described Item 1,
- wherein the change acquisition unit acquires a first change rate that is a change rate of the fluorescence signal within the first time range detected by the fluorescence detection unit, as the change degree of the fluorescence signal, and
- wherein the determination unit determines that the progress of the treatment is in the steady state, based on that the first change rate has fallen within a change rate range as the predetermined range of the change degree (Item 3)

The treatment support device as recited in the above-described Item 2,
- wherein the determination unit determines that the progress of the treatment is in the steady state, based on a fact that the first change rate has become near zero.

(Item 4)

The treatment support device as recited in the above-described Item 2 or 3,
- wherein the first time range includes a present time within the treatment time,
- wherein the change acquisition unit calculates the first change rate and a second change rate that is a change rate of the fluorescence signal detected by the fluorescence detection unit, within a second time range including a time before the first time range within the treatment time including the first time range, and
- wherein the determination unit determines whether or not the progress of the treatment is in the steady state, based on a comparison between the first change rate and the second change rate.

(Item 5)

The treatment support device as recited in the above-described Item 4,
wherein the second time range is a time range separated from the first time range within the treatment time including the first time range.

(Item 6)

The treatment support device as recited in the above-described Item 4 or 5,
wherein the determination unit determines that the progress of the treatment is in the steady state, based on a fact that the first change rate has fallen within the change rate range as the predetermined range of the change degree and that a ratio between the first change rate and the second change rate has fallen within a predetermined rate ratio range.

(Item 7)

The treatment support device as recited in any one of the above-described Items 1 to 6,
wherein the predetermined operation to be performed by control of the operation control unit when it is determined by the determination unit that the progress of the treatment is in the steady state includes an operation of notifying a user that the progress of the treatment is in the steady state.

(Item 8)

The treatment support device as recited in the above-described Item 7, further comprising:
a display unit configured to display the change degree of the fluorescence signal within the first time range,
wherein the operation of notifying the user that the progress of the treatment is in the steady state includes an operation of changing a display method of a display indicating the change degree of the fluorescence signal in the display unit before and after determined by the determination unit that the progress of the treatment is in the steady state.

(Item 9)

The treatment support device as recited in any one of the above-described Items 1 to 8,
wherein the predetermined operation performed by the control of the operation control unit when it is determined by the determination unit that the progress of the treatment is in the steady state includes an operation of stopping irradiation of the treatment light by the irradiation unit.

(Item 10)

The treatment support device as recited in any one of the above-described Items 1 to 9, further comprising:
an analysis unit configured to analyze the fluorescence signal detected by the fluorescence detection unit; and
a control unit configured to control the irradiation of the treatment light by the irradiation unit,
wherein the analysis unit includes the change acquisition unit, the determination unit, and the operation control unit, and
wherein the operation control unit performs control of stopping the irradiation of the treatment light by the irradiation unit via the control unit, as the predetermined operation.

The invention claimed is:

1. A treatment support device comprising:
an irradiation unit configured to irradiate a medical agent with treatment light in treatment for killing cancer cells by irradiating the medical agent with the treatment light of a predetermined wavelength, the medical agent including a fluorescent material administered to a body of a subject;
a fluorescence detector configured to detect fluorescence emitted by the fluorescent material of the medical agent excited by irradiation of the treatment light;
a change calculator configured to acquire a change degree of a fluorescence signal detected by the fluorescence detector in a first time range within a treatment time;
a determination calculator configured to determine whether or not a progress of the treatment is in a steady state, based on at least a fact that the change degree of the fluorescence signal within the first time range acquired by the change calculator has fallen within a predetermined range of the change degree; and
an operation controller configured to control a predetermined operation related to a fact that the treatment is in the steady state when it is determined by the determination calculator that the progress of the treatment is in the steady state.

2. The treatment support device as recited in claim 1,
wherein the change calculator acquires a first change rate that is a change rate of the fluorescence signal within the first time range detected by the fluorescence detector, as the change degree of the fluorescence signal, and
wherein the determination calculator determines that the progress of the treatment is in the steady state, based on that the first change rate has fallen within a change rate range as the predetermined range of the change degree.

3. The treatment support device as recited in claim 2,
wherein the determination calculator determines that the progress of the treatment is in the steady state, based on a fact that the first change rate has become near zero.

4. The treatment support device as recited in claim 2,
wherein the first time range includes a present time within the treatment time,
wherein the change calculator calculates the first change rate and a second change rate that is a change rate of the fluorescence signal detected by the fluorescence detector in a second time range within the treatment time,
wherein the second time range is a time range separated from the first time range or partially overlapped with the first time range,
wherein the second time range includes at least a time before the first time range within the treatment time, and
wherein the determination calculator determines whether or not the progress of the treatment is in the steady state, based on a comparison between the first change rate and the second change rate.

5. The treatment support device as recited in claim 4,
wherein the second time range is a time range separated from the first time range, within the treatment time including the first time range.

6. The treatment support device as recited in claim 4,
wherein the determination calculator determines that the progress of the treatment is in the steady state, based on a fact that the first change rate has fallen within the change rate range as the predetermined range of the change degree and that a ratio between the first change rate and the second change rate has fallen within a predetermined rate ratio range.

7. The treatment support device as recited in claim 1,
wherein the predetermined operation to be performed by control of the operation controller when it is determined by the determination calculator that the progress of the treatment is in the steady state includes an operation of notifying a user that the progress of the treatment is in the steady state.

8. The treatment support device as recited in claim 7, further comprising:
a display unit configured to display the change degree of the fluorescence signal within the first time range,
wherein the operation of notifying the user that the progress of the treatment is in the steady state includes an operation of changing a display method of a display indicating the change degree of the fluorescence signal in the display unit before and after determined by the determination calculator that the progress of the treatment is in the steady state.

9. The treatment support device as recited in claim 7, further comprising:
an analysis unit configured to analyze the fluorescence signal detected by the fluorescence detector; and
a control unit configured to control the irradiation of the treatment light by the irradiation unit,
wherein the analysis unit includes the change calculator, the determination calculator, and the operation controller, and
wherein the operation controller performs control of stopping the irradiation of the treatment light by the irradiation unit via the control unit, as the predetermined operation.

10. The treatment support device as recited in claim 1,
wherein the predetermined operation performed by the control of the operation controller when it is determined by the determination calculator that the progress of the treatment is in the steady state includes an operation of stopping irradiation of the treatment light by the irradiation unit.

* * * * *